(12) United States Patent
Lawman et al.

(10) Patent No.: US 7,348,015 B2
(45) Date of Patent: Mar. 25, 2008

(54) ANTIGEN MODIFIED CANCER CELL VACCINES FOR CANCER THERAPY

(75) Inventors: Michael J. P. Lawman, Tampa, FL (US); Patricia D. Lawman, Tampa, FL (US)

(73) Assignee: Morphogenesis, Inc., Tampa, FL (US)

( * ) Notice: Subject to any disclaimer, the term of this patent is extended or adjusted under 35 U.S.C. 154(b) by 178 days.

(21) Appl. No.: 10/964,471

(22) Filed: Oct. 13, 2004

(65) Prior Publication Data

US 2005/0106130 A1 May 19, 2005

Related U.S. Application Data

(63) Continuation-in-part of application No. 10/652,578, filed on Aug. 29, 2003, now Pat. No. 7,094,603, which is a continuation of application No. 09/950,374, filed on Sep. 10, 2001, now abandoned, which is a continuation of application No. 09/394,226, filed on Sep. 13, 1999, now abandoned, which is a continuation of application No. PCT/US99/00787, filed on Jan. 14, 1999.

(60) Provisional application No. 60/071,497, filed on Jan. 14, 1998, now abandoned.

(51) Int. Cl.
*A61K 39/00* (2006.01)
*A61K 45/00* (2006.01)
*C12N 15/00* (2006.01)

(52) U.S. Cl. ............................ 424/244.1; 435/320.1; 435/252.3; 435/69.3; 435/71.1; 435/243; 536/23.7

(58) Field of Classification Search ...................... None
See application file for complete search history.

(56) References Cited

U.S. PATENT DOCUMENTS 5,736,388 A 4/1998 Chada et al.
6,774,119 B1 8/2004 Wechsler et al.

FOREIGN PATENT DOCUMENTS

| EP | 0569678 | 11/1993 |
|---|---|---|
| WO | WO 93/24136 | 12/1993 |
| WO | WO 94/21808 | 9/1994 |
| WO | WO 95/00178 | 1/1995 |
| WO | WO 95/13092 | 5/1995 |
| WO | WO 96/29093 | 9/1996 |
| WO | WO 96/36366 | 11/1996 |
| WO | WO 97/00085 | * 1/1997 |

OTHER PUBLICATIONS

Carbone et al., Multistep and multifactorial carcinogenesis: when does a contributing factor become a carcinogen?Semin Cancer Biol. Dec. 2004;14(6):399-405. Review.*

Keith et al., Multicomponent therapeutics for networked systems. Nat Rev Drug Discov. Jan. 2005;4(1):71-8. Review.*
Van Dyke et al., Cell, 2002, 108: 135-144.*
Tomai et al., Superantigenicity of Streptococcal M protein, 1990, The Journal of experimental medicine, 172:359-362.*
Biochemistry John Wiley and Sons, 1990, 126-128.*
Lawman et al., 2005, J. Immunotherapy 28:614-615 Abstract.*
Avery, A.C. et al. "Activation of T Cells by Superantigen in Class II-Negative Mice" *J. Immunol.*, 1994, pp. 4855-4861, vol. 153.
Banchereau, J. et al. "Dendritic Cells and the Control of Immunity" Nature, 1998, pp. 245-252, vol. 392.
Barratt-Boyes, S.M. et al. "Studies in a Chimpanzee Model of Dendritic Cell-Based Cancer Vaccines" Proceedings of the 87th, Annual Meeting of the American Association for Cancer, 1996, XP002039146 (abstract only).
Boyle, Michael D.P. et al. "Analysis of Genes Encoding Two Unique Type IIa Immunoglobulin G-Binding Proteins Expressed by a Single Group A Streptococcal Isolate" *Infection and Immunology*, 1994, pp. 1336-1347, vol. 62, No. 4.
Boyle, Michael D.P. et al. "Characterization of A Gene Coding for A Type IIo Bacterial IgG-Binding Protein" *Molecular Immunology*, 1995, pp. 669-678, vol. 32, No. 9.
Dellabona, Paolo et al. "Superantigens Interact With MHC Class II Molecule Outside of the Antigen Groove" *Cell*, 1990, pp. 1115-1121, vol. 62.
Dohlsten, M. et al. "Monoclonal Antibody-Targeted Superantigens: A Different Class of Anti-Tumor Agents" *Proc. Natl. Acad. Sci. USA*, 1991, pp. 9287-9291, vol. 88.
Dohlsten, M. et al. "Human Major Histocompatibility Complex Class II-Negative Colon Carcinoma Cells Present Staphylococcal Superantigens to Cytotoxic T Lymphocytes: Evidence for a Novel Enterotoxin Receptor" *Eur. J. Immunol.*, 1991, pp. 1229-1233, vol. 21.
Dohlsten, M. et al. "Role of the Adhesion Molecule ICAM-1 (CD54) in Staphylococcal Enterotoxin-Mediated Cytotoxicity" *Eur. J. Immunol.*, 1991, pp. 131-135, vol. 21.
Fleischer, B., et al. "T-Lymphocyte Stimulation by Microbial Superantigens" *Chem. Immunol.*, 1992, pp. 36-64, vol. 55.
Fraser, James D. et al. "CD28 and T Cell Antigen Receptor Signal Transduction Coordinately Regulate Interleukin 2 Gene Expression in Response to Superantigen Stimulation" *J. Ex. Med.*, 1992, pp. 1131-1134, vol. 175.
Gilboa, Eli et al., Immunotherapy of Cancer With Dendritic-Cell Based Vaccines *Cancer Immunol Immunother*, 1998, pp. 82-87, vol. 46, No. 2.
Hartwig, Udo F. et al. "Mutations Affecting MHC Class II Binding of the Superantigen Streptococcal Erthrogenic Toxin A" *International Immunology*, 1993, pp. 869-875, vol. 5, No. 8.

(Continued)

*Primary Examiner*—Joseph Woitach
*Assistant Examiner*—Maria Leavitt
(74) *Attorney, Agent, or Firm*—Saliwanchik, Lloyd & Saliwanchik

(57) ABSTRACT

Disclosed are methods for treating cancers, particularly tumorigenic types. Cancer cells are modified to express highly immunogenic antigens so that the cells will generate a defensive response in a mammal that exhibits the cancer or is predisposed to cancer and prevent or ameliorate proliferation of cancer cells. The novel cancer cell vaccines are expected to be effective against a wide range of tumors and leukemias.

13 Claims, 13 Drawing Sheets

OTHER PUBLICATIONS

Herman, Andrew et al. "Identification of the Staphylococcal Enterotoxin A. Superantigen Binding Site in the β1 Domain of the Human Histocompatibiity Antigen HLA-DR", *Proc. Natl. Acad. Sci. USA*, 1991, pp. 9954-9958, vol. 88.

Hermann, Thomas et al. "Staphylococcal Enterotoxin-Dependent Lysis of MHC Class II Negative Target Cells by Cytolytic T Lymphocytes", *J. Immunol.*, 1991, pp. 2504-2512, vol. 146.

Hock, Randy A. et al. "Murine Neuroblastoma Vaccines Produced by Retroviral Transfer of MHC Class II Genes", *Cancer Gene Therapy*, 1996, pp. 314-320, vol. 3, No. 5.

Johnson, Howard M. et al. "Superantigens in Human Disease", *Scientific American*, 1992, pp. 92-111.

Karp, David R. et al. "The α1 Domain of the HLA-DR Molecule is Essential for High-Affinity Binding of the Toxic Shock Syndrome Toxin-1", *Nature*, 1990, pp. 474-476, vol. 346.

Menard, S. et al. "Mycobacterium Tuberculosis Gene Transfer in Melanoma Cells Induces Antitumoral Immunity in Mice" *Cancer Gene Therapy*, 1995, p. 318, vol. 2, No. 4.

Mayordoma, J.I. et al. "Bone Marrow-Derived Dendritic Cells Pulsed With Synthetic Tumour Peptides Elicit Protective and Therapeutic Antitumour Immunity", *Nature Medicine*, 1995, pp. 1297-1302, vol. 1, No. 12.

Mollick, Joseph A. et al. "Staphylococcal Exotoxin Activation of T Cells", *J. Immunology*, 1991, pp. 463-468, vol. 146.

Panina-Bordignon, Paola et al. "Identification of HLA-DRα Chain Residues Critical for Binding of the Toxic Shock Sydrome Toxin Superantigen", *J. Exp. Med.*, 1992, pp. 1779-1784, vol. 176.

Rust, Chantal, J.J. et al. "Specific Recognition of Staphylococcal Enterotoxin A by Human T Cells Bearing Receptors With the Vγ9 Region", *Nature*, pp. 572-574, vol. 346, 1990.

Webb, Susan R. et al. "T-cell Activation by Superantigens", *Curr Opinion in Immun.*, 1994, pp. 467-475, vol. 6.

Tomai, M. et al. "Superantigenicity of Streptococcal M Protein", *J. Exp. Med.*, 1990, pp. 359-362, vol. 172.

Fleischer, B. et al. "Superantigens and Pseudosuperantigens of Gram-Positive Vocci", *Med. Microbiol. Immumol.*, pp. 108, vol. 184, 1995.

Degnan, B. et al. "Streptococcus pyogenes Type 5 M Protein is an Antigen, Not a Superantigen, for Human T Cells", *Human Immunology*, 1997, pp. 206-215, vol. 53.

Esaki, Y. et al. "Role of Human Major Histocopatibility Complex DQ Molecules in Superantigenicity of Streptococcus-Derived Protein", *Infection and Immunity*, 1994, pp. 1228-1235, vol. 62, No. 4.

Verma, I.M. et al. "Gene Therapy—Promises, Problems and Prospects", *Nature*, 1997, pp. 239-242, vol. 389.

Gomez-Navarro, J. et al. "Gene Therapy for Cancer", *Eur. J. Cancer*, 1999, pp. 867-885, vol. 35, No. 6.

Ngo, J.T. et al. "Computational Complexity, Protein Structure Prediction, and the Levinthal Paradox", *The Protein Folding Problem and Tertiary Structure Prediction*, 1994, p. 433 and 492-495, Merz (ed.) Birkhauser, Boston, MA.

Chiu, T-L et al. "Optimizing Energy Potentials for Success in Protein Tertiary Structure Prediction", *Folding & Design*, May 1998, pp. 223-228, vol. 3.

Orkin, S.H. et al. "Report and Recommendations of the Panel to Assess the NIH Investment in Research on Gene Therapy", Dec. 1995, pp. 1-41.

Ross, G. et al. "Gene Therapy in the United States: A Five Year Status Report", *Human Gene Therapy*, Sep. 1996, pp. 1781-1790, vol. 7.

Ostrand-Rosenberg, S. et al. "Tumor-Specific Immunity Can Be Enhanced by Transfection of Tumor Cells with Syngeneic MHC-Class-II Genes or Allogeneic MHC-Class-I Genes", *Int. J. Cancer*, 1991, pp. 61-68, vol. 6.

Kalland, T. et al. "Targeting of Superantigens", *Cell Biophysics*, 1993, pp. 147-164, vol. 22.

Coupar, B.E.H. et al. "A General Method for the Construction of Recombinant Vaccinia Viruses Expressing Multiple Foreign Genes", *Gene*, 1988, pp. 1-10, vol. 68.

Eck, S.L. et al. "Scope of Gene Therapy", *Gene-Based Therapy*, pp. 77-101, Chapter 5, 1996.

Marshall, E. "Gene Therapy's Growing Pains", *Science*, Aug. 1995, pp. 1050-1055, vol. 269.

Hollingshead, S.K. et al. "Molecular Evolution of a Multigene Family in Group A Streptococci", *Mol. Biol. Evol.*, 1994, pp. 208-219, vol. 11, No. 2.

Hollingshead, S.K. et al. "Structural Heterogeneity of the Emm Gene Cluster in Group A Streptococci", *Mol. Microbiol.*, May 1993, pp. 707-717, vol. 8, No. 4.

Ji, Y. et al. "Intranasal Immunization with C5a Peptidase Prevets Nasopharyngeal Colonization of Mice by the Group A Streptococcus", *Infection and Immunity*, Jun. 1997, pp. 2080-2087, vol. 65, No. 6.

Bessen, D. et al. "Passive Acquired Mucosal Immunity to Group A Streptococci by Secretary Immunoglobulin A", *J. Exp. Med.*, Jun. 1988, pp. 1945-1950, vol. 167, No. 6.

Yamaguchi, Y. et al. "Adoptive immunotherapy of cancer using activated autologous lymphocytes—current status and new strategies", *Hum Cell*. Dec. 2003; 16 (4):183-9.

Cranmer, LD. et al. "Clinical applications of dendritic cell vaccination in the treatment of cancer", *Cancer Immunol Immunother*, Apr. 2004; 53(4):275-306. Epub Nov. 26, 2003.

Wallack, MK. et al. "A phase III randomized, double-blind multiinstitutional trial of vaccinia melanoma oncolysate-active specific immunotherapy for patients with stage II melanoma", *Cancer*, Jan. 1, 1995;75 (1):34-42.

Giantonio, BJ. et al. "Superantigen-based immunotherapy: a phase I trial of PNU-214 a monoclonal antibody-staphylococcal enterotoxin A recombinant fusion protein, in advanced pancreatic and colorectal cancer", *J. Clin. Oncol.*, May 1997; 15(5):1994-2007.

* cited by examiner

```
Consensus        CTGTGGAATG TGTGTCAGTT AGGGTGTGGA AAGTCCCCAG GCTCCCCAGC         50
emml55/pSVK3     CTGTGGAATG TGTGTCAGTT AGGGTGTGGA AAGTCCCCAG GCTCCCCAGC         50

Consensus        AGGCAGAAGT ATGCAAAGCA TGCATCTCAA TTAGTCAGCA ACCAGGTGTG        100
emml55/pSVK3     AGGCAGAAGT ATGCAAAGCA TGCATCTCAA TTAGTCAGCA ACCAGGTGTG        100

Consensus        GAAAGTCCCC AGGCTCCCCA GCAGGCAGAA GTATGCAAAG CATGCATCTC        150
emml55/pSVK3     GAAAGTCCCC AGGCTCCCCA GCAGGCAGAA GTATGCAAAG CATGCATCTC        150

Consensus        AATTAGTCAG CAACCATAGT CCCGCCCCTA ACTCCGGCCCA TCCCGCCCCT        200
emml55/pSVK3     AATTAGTCAG CAACCATAGT CCCGCCCCTA ACTCCGCCCA TCCCGCCCCT        200

Consensus        AACTCCGCCC AGTTCCGCCC ATTCTCCGCC CCATGGCTGA CTAATTTTTT        250
emml55/pSVK3     AACTCCGCCC AGTTCCGCCC ATTCTCCGCC CCATGGCTGA CTAATTTTTT        250

Consensus        TTATTTATGC AGAGGCCGAG GCCGCCTCGG CCTCTGAGCT ATTCCAGAAG        300
emml55/pSVK3     TTATTTATGC AGAGGCCGAG GCCGCCTCGG CCTCTGAGCT ATTCCAGAAG        300

Consensus        TAGTGAGGAG GCTTTTTTGG AGGCCTAGGC TTTTGCAAAA AGCTATCGAA        350
emml55/pSVK3     TAGTGAGGAG GCTTTTTTGG AGGCCTAGGC TTTTGCAAAA AGCTATCGAA        350
second sec (1-184)                                   TTTGCAAAAA AGCTATCGAA         19

Consensus        TTAATACGAC TCATTATAGG GAGATCGAAT TCGGCWTGGC TAAAAATACC        400
emml55/pSVK3     TTAATACGAC TCATTATAGG GAGATCGAAT TC--ATGGC TAAAAATACC        400
second sec (1-184) TTAATACGAC TCATTATAGG GAGATCGAAT TCGGCTTGGC TAAAAATACC        69

Consensus        ACGAATAGAC ACKATTCGCT TAGAAAATTA AAAACAGGAA CGGCTTCAGT        450
emml55/pSVK3     ACGAATAGAC ACGATTCGCT TAGAAAATTA AAAACAGGAA CGGCTTCAGT        450
second sec (1-184) ACGAATAGAC ACTATTCGCT TAGAAAATTA AAAACAGGAA CGGCTTCAGT       119
```

FIG. 4A

| | | | | | |
|---|---|---|---|---|---|
| Consensus | AGCAGTAGCT | TTGACTGTTT | TTGGGACAGG | ACTGGTAGCA | GGGCAGACAG | 500 |
| emml55/pSVK3 | AGCAGTAGCT | TTGACTGTTT | TTGGGACAGG | ACTGGTAGCA | GGGCAGACAG | 500 |
| second sec (1-184) | AGCAGTAGCT | TTGACTGTTT | TTGGGACAGG | ACTGGTAGCA | GGGCAGACAG | 169 |
| Consensus | TAAAAGCAAA | CCAAACAGAA | CCATCTCAGA | CCAATAACAG | ATTATATCAA | 550 |
| emml55/pSVK3 | TAAAAGCAAA | CCAAACAGAA | CCATCTCAGA | CCAATAACAG | ATTATATCAA | 550 |
| second sec (1-184) | TAAAAGCAA | | | | | 219 |
| Consensus | GAAAGACAAC | GTTTACAGGA | TTTAAAAAGT | AAGTTTCAAG | ACCTGAAAAA | 600 |
| emml55/pSVK3 | GAAAGACAAC | GTTTACAGGA | TTTAAAAAGT | AAGTTTCAAG | ACCTGAAAAA | 600 |
| Consensus | TCGTTCAGAG | GGATACATTC | AGCAATACTA | CGACGAAGAA | AAGAACAGTG | 650 |
| emml55/pSVK3 | TCGTTCAGAG | GGATACATTC | AGCAATACTA | CGACGAAGAA | AAGAACAGTG | 650 |
| Consensus | GAAGTAACTC | TAACTGGTAC | GCAACCTACT | TAAAAGAATT | AAATGACGAA | 700 |
| emml55/pSVK3 | GAAGTAACTC | TAACTGGTAC | GCAACCTACT | TAAAAGAATT | AAATGACGAA | 700 |
| Consensus | TTTGAACAAG | CTTATAATGA | ACTTAGTGGT | GATGGTGTAA | AAAAATTAGC | 750 |
| emml55/pSVK3 | TTTGAACAAG | CTTATAATGA | ACTTAGTGGT | GATGGTGTAA | AAAAATTAGC | 750 |
| Consensus | TGCAAGTTTG | ATGGAAGAAA | GAGTCGCTTT | AAGAGACGAA | ATCGATCAGA | 800 |
| emml55/pSVK3 | TGCAAGTTTG | ATGGAAGAAA | GAGTCGCTTT | AAGAGACGAA | ATCGATCAGA | 800 |
| Consensus | TTATGAAAAT | ATCAGAAGAA | TTAAAAAATA | AGCTGAGAGC | AACAGAAGAA | 850 |
| emml55/pSVK3 | TTATGAAAAT | ATCAGAAGAA | TTAAAAAATA | AGCTGAGAGC | AACAGAAGAA | 850 |

FIG. 4B

ANTIGEN MODIFIED CANCER CELL VACCINES FOR CANCER THERAPY

CROSS-REFERENCE TO RELATED APPLICATIONS

This application is a continuation in part of U.S. application Ser. No. 10/652,578 filed Aug. 29, 2003, now U.S. Pat. No. 7,094,603 which is a continuation of U.S. application Ser. No. 09/950,374 filed Sep. 10, 2001, now abandoned which is a continuation of U.S. Ser. No. 09/394,226 filed Sep. 13, 1999, now abandoned which is a continuation of International Application No. PCT/US99/00787, filed Jan. 14, 1999, which claims priority from U.S. Provisional Application Ser. No. 60/071,497, filed Jan. 14, 1998, now abandoned.

BACKGROUND OF THE INVENTION

Cancer is the second most common disease and also one of the most feared. Cancer occurs when cells continue to divide and fail to die at the appropriate time. Under normal circumstances, the many types of cells that make up the body grow and divide to produce more cells as they are needed in order to maintain a healthy body. Tumors may form when this orderly process is disrupted by changes in genes that control normal cell growth and death and cellular growth becomes uncontrolled. Genetic changes that arise internally due to defective DNA repair or may be induced by external factors such as diet, exposure to ultraviolet or other types of ionizing radiation, viruses such as cervical papillomaviruses, exposure to chemical carcinogens in the workplace or in the environment, drug or tobacco use, or to agents such as asbestos. Some detrimental genetic alterations are inherited.

Regardless of which particular combination of insults and accidents contribute to the root cause of cancer, cumulative mutations in cells can arise from alterations in specific locations in the DNA of the cell. Pieces of chromosomes may become scrambled, truncated or fused together; or entire chromosomes may be lost or duplicated in their entirety. As a result of these alterations cancer cells proliferate more rapidly than neighboring normal cells. The cell abnormalities are passed down to their cellular descendants as these clonal armies continue to grow unabated. They eventually develop the capacity through additional mutations to invade and destroy surrounding tissue. Malignant cancers usually become life-threatening because they develop the power to disable the regulatory mechanisms that confine them to the specific tissue in which they arose so that they disengage from the malignant tumor and travel through the bloodstream or lymphatic system where they eventually interfere with vital systems.

Current Cancer Therapies

New and effective cancer treatments are constantly being sought. The most common therapies include radiation and drug treatments, many of which are toxic and harmful to normal cells. Conventional therapies may kill the majority of cells within a tumor but a small number of unaffected cells may be able to reestablish the aberrant pattern of proliferation.

While most malignant cells appear to be highly susceptible to current cancer treatments, there is some speculation that a certain subset of cells, perhaps stem cells, are more resistant to drugs and radiation than normal, non-cancerous cells. Alternatively, tumor cells may simply develop resistance to chemical and radiation treatments, leading to recurrence of chemo- and/or radio-resistant cancers because the resistant cells maintain their ability to proliferate indefinitely. Resistance may also develop because administration of chemotherapeutic agents for the treatment of tumors is restricted by the toxicity of these agents to normal cells.

Gene Therapy

One approach to lowering toxicity of high drug doses is transfection of healthy, normal stem cells with transgenes that confer resistance to these agents. In theory, this will result in cytotoxic drug-resistant cells and allow the administration of higher, therapeutically significant doses of chemotherapeutic agents. Use of transfected cells has been suggested for protection of bone marrow cells since bone marrow cells are rapidly dividing and thereby most at risk to chemotoxicity and in fact has shown some success in animal models, Licht et al., 2000.

Recently, gene therapy methods have been explored both as cancer diagnostics and as cancer treatments. Because most forms of cancer are complex, multifactorial, and multigenic in nature, many conceptual and technical obstacles remain to be overcome in order to approach this disease at the genetic level. Yet, it is the molecular nature of tumorigenesis, i.e., the activation of dominant oncogenes and/or the inactivation of tumor suppressor genes, which provides insight for such strategies in that these genetic events represent novel targets for molecular therapy. Genetic analysis is already being used in diagnostic and prognostic predictions in certain malignancies; e.g., amplification of erb-B2 in breast and ovarian cancer; amplification of N-myc in neuroblastoma; and ras mutations in adenocarcinoma of the lung.

Unfortunately, the list of oncogenes and tumor suppressor genes continues to grow. Recently, mutations in at least 15 tumor suppressor genes were identified and the number of oncogenes now exceeds 100 (Gibbs, et al., 2004). The consequences remain uncertain, but the evidence points to the possibility that each tumor may be unique in its genetic disarray. If this is true, the prospect of tracking the root causes, categorizing the distinguishing marks of a particular cancer as well as determining early diagnoses and accurate prognostic evaluations become exponentially more difficult, and the chance even more remote of finding a treatment specific for each tumor.

Compounding this complexity, researchers are now finding that whereas an individual tumor may begin its life of malignancy with a particular accumulation of mutations in a single cell, which then passes down its genetic abnormalities to its descendants, the tumor itself is comprised of a large diversity of cells. Although all these cells are very different from normal human cells, they are not the masses of identical clones as once believed. In fact, there seems to be a small subset of cells within each tumor that is responsible for not only the growth of the tumor but for its metastasis.

Despite some progress in developing gene therapy methods, use of these methods in the treatment of cancer still has several obstacles to overcome. In vivo treatments for malignant melanoma in dogs, for example, has met with some success, showing a positive response to tumor regression over a period of 6-12 weeks after a direct DNA injection encoding a *Staphylococcus* antigen and GM-CSF cytokine (WO96/36366). Liposome/Staphylcoccal antigen injections alone, however, failed to show any effect even after 17 weeks, suggesting that tumor regression was caused by a toxic effect generated by the cytokine or cytokine/antigen combination in the cancer cells.

The use of "informational drugs," a type of gene therapy, has also been proposed. Antisense oligonucleotides, small synthetic nuclease-resistant nucleotide sequences complementary to specific RNA sequences, are an example of this type of drug. By specifically binding and thereby inhibiting transcription and/or translation of a single oncogene, it may be possible to block oncogenesis and even reverse clinical symptoms. Unfortunately, the efficacy of informational drugs seems to depend on their use with other drugs. Limited effectiveness has been observed in a study of melanoma patients using an antisense molecule in combination with dacarbazine. Some progress is being made in targeted antisense oligonucleotide therapy; for example, it was reported that therapeutic effectiveness of the cancer therapeutic agent trinotecan in mice was increased by administration of an antisense molecule tarteted to RIalpha subunit of campdependent protein kinase (Wang, et al., Int. J. Oncol. Jul. 21, 2002 (1), 73-80). However, antisense application has yet to live up to the expectation of being widely applicable for all types of cancers.

Immunotherapy

The manipulation of the host immune system to identify cancer cells as non-self; i.e., methods to mobilize and strengthen the immune system so that it can selectively destroy and/or inhibit proliferation of cancerous cells, is gaining more attention. This is due to the recognition that the host itself may be able to generate the safest and most effective defense against cancer.

Large numbers of people are exposed to carcinogens every day; yet only a tiny minority suffer life-threatening tumors. Given so many opportunities for aberrant cells to arise, it is remarkable that most hosts do not inevitably succumb to cancer. Clearly, the most effective solution is to eliminate cancerous cells before they have the chance to cycle out of control.

Immunologists are in general agreement that the body is capable of protecting itself from cancer. Historically, it was postulated that the transformation of normal tissues into neoplasms was accompanied by the expression of new molecules, i.e., tumor-specific antigens. Early studies attempted to prove the existence of tumor-associated antigens by transplanting tumors from one animal to another and found that the tumors were rejected. The rejection was wrongly attributed to the presence of neo-antigens instead of disparate histocompatibility antigens, as is known today.

The vast majority of malignancies arise in immunocompetent hosts, raising doubts as to whether a general strengthening of the immune system can ever be effective in targeting cancer cells, which are not always recognized as foreign by the host. It is now known that tumor cells do indeed carry antigens that are different from their normal counterparts. These antigens can be tumor-associated or tumor-specific. Tumor-associated antigens can be generated by the activation of normally repressed genes, such as oncofetal antigens which are normally synthesized during embryogenesis but are not found on adult cells; some are present but are masked; some molecules may be lost when the cells become transformed and thus alter the profile of adjacent molecules by their absence; some antigens may be modifications of normal molecules; and some may be nuclear or cytoplasmic and thus hidden from immune surveillance. Tumor-specific antigens are restricted to tumor tissues. They are not found in normal adult or fetal tissues and are rare.

In order for an immunotherapy to be effective, evasive techniques used by tumor cells must be overcome. Some therapies under investigation administer chemical messengers such as cytokines like IL-2 and IL-12 alone or in combination, lymphocytes specific for telomerase, bacterial extracts from *Corynebacterium granulosum* as adjuvants, or drugs which boost the immune system. These are aimed at heightening the immune response in general. In an attempt to make the immune response more specific for the tumor cells, some employ the use of autologous tumor cells, either combined with cytokines such as GM-CSF, gamma interferon or IL-2, individually or in combination, or transfected with the genes that encode these cytokines. A similar approach utilizes tumor cell lines instead of autologous tumor cells.

Antigens, bacterial and viral, have also been used in combination with cytokine or other immunomodulator genes delivered by means of adenovirus, retrovirus or plasmid vectors (WO 94/21808; WO 96/29093). The presence of cytokines is a factor in the relative success of some of these approaches. In some cases, a highly destructive and specific response to otherwise nonimmunogenic tumors can be elicited by the insertion of genes encoding interleukin-2, interleukin-4, interleukin-12, interferon-γ, interferon-α and/or tumor necrosis factor into the tumor cells as well as into cytotoxic lymphocytes or macrophages, although can serious side-effects can be caused at high doses.

Several approaches use bio-signals to direct immune effector cells to the tumor in a non-specific manner. Other approaches focus on the immune cells themselves. Autologous antigen presenting cells, including dendritic cells have been loaded with tumor, with cytokines and/or with total tumor RNA in an effort to make the immune response more specific for the tumor (Cranmer, et al., 2004).

Oncophages have been used to lyse autologous tumor cells in the hope of generating a tumor-specific response or have transfected tumor cells with immunotoxins (Wallack, et al., 1995). Patients also have been vaccinated with specific tumor antigens, tumor-specific monoclonal antibodies, HSP 70 purified from autologous tumor cells, autologous T cells activated against tumor cells ex vivo. These methods focus on specific aspects of the immune response to particular tumor characteristics.

Some immunotherapeutic modalities are based on studies in which tumor cells are transfected with genes encoding Major Histocompatibility Complex (MHC) (Hock et al., 1996; EP 569678; WO 95/13092), Calmette-Guérin (BCG) (Morton, et al., 1992) and *Mycobacterium* (Menard et al., 1995) antigens. However, despite promising results when compared with control groups, the significant survival advantage conferred by systemically administered antigen such as BCG was not confirmed in concurrently controlled randomized clinical trials.

Autologous tumor-infiltrating lymphocytes have been used in genetic immuno-modulation studies because of their inherent specificity for the tumor and their ability to home back to the tumor site when reinfused into the patient. Normal tissue has been protected by stably transfecting normal bone marrow cells with cytokine genes prior to chemotherapy, thereby achieving a more continuous effect while obviating the need to infuse drugs which have short half-lives and produce systemic side effects when delivered intravenously (Yamaguchi, et al., 2003).

T-lymphocytes recognize at least two different types of antigens; peptides derived from conventional protein antigens, and the so-called "superantigens". The classical definition for superantigen is a polypeptide that reacts in some ways like conventional antigens but exhibits critical differences in others (Johnson et al., 1992). Before a T helper cell can recognize conventional protein antigens, these proteins must first undergo processing by macrophages or other antigen presenting cells (APCs). APCs then display the peptide on the cell surface in combination with MHC. Unlike typical antigens, however, the distinguishing feature of superantigens according to Johnson et al., (1992) is the ability to bind MHC directly, to specific Vβ segments of TCR that are outside of the normal antigen-binding groove, without uptake and processing by APCs. Some examples of superantigens include the soluble exotoxins produced by gram-positive bacteria such as *Staphylococcus aureus*, which typify bacterially-derived superantigens, and viral superantigens such as those encoded by endogenous mouse mammary tumor viruses.

Conjugation between the superantigen staphylococcal enterotoxin-A (SEA), and mAbs recognizing human colon cancer enables T cells to lyse colon carcinoma cells in vitro (Giantonio, et al., 1997). Staphylococcal enterotoxins have been suggested as possible cancer vaccine candidates (WO 95/0178). However, there is no evidence that transfected cells produce a sufficient in vivo immune response in human cancer patients. Likewise, induction of a T-cell response is described in WO 96/36366 where after repeated administration, genes encoding SEA and a cytokine were effective in causing regression or slowing growth of a canine melanoma of the composition. Administering the superantigen alone was ineffective.

Deficiencies in the Art

No general method for treating cancers has yet been developed or have productive methods been suggested. The search continues to find treatments that cure and/or arrest and prevent the many types of tumors and leukemias that affect individual health as well as economic issues. Advantages of immunotherapy are considerable when compared to standard treatments in that little or no toxicity has been seen in clinical trials thus far, and vaccine-induced regression, when achieved, is usually durable, often lasting from months to years. However, past efforts to marshal host defenses by stimulating an immune response to specific cancers have generally failed, despite use of immunostimulatory and gene therapy methods.

Therapies are needed that will effectively address controlling and/or curing of a wide range of cancers and do not suffer some of the disadvantages of high toxicity encountered with current radiation and chemotherapy regimes. An effective cancer vaccine, for example, must elicit both humoral (antibody) and appropriate cellular (antigen-specific T cell) responses. While some viral antigens expressed in tumor cells activate both these arms of the immune system, the response is so rapid that the genetically modified tumor cells were eliminated before T cells reactive to the tumor itself could be developed. Despite decades of effort and dozens of different approaches, no immunotherapy has emerged as a standard therapy for any type of cancer. There is therefore an unmet need to find ways to control and eliminate cancer cells in vivo without toxic effects and provide permanent protection against a wide range of cancers.

BRIEF SUMMARY OF THE INVENTION

The present invention is the discovery of a novel and effective cancer cell vaccine. The cell vaccine was developed by engineering cancer cells to express antigens capable of inducing tumor-protective immunity. The modified cancer cells are highly immunogenic to the host and can be administered to patients suffering from the cancer or to patients in need of a protective vaccine.

As used herein, antigens expressed in the modified cancer cells of the invention are referred to as "initiating" or "priming" antigens, and may include antigens more generally referred to as "superantigens." It is well known in the art that malignant tumors express tumor-associated and tumor-specific antigens, which should make them targets for the immune system of the host.

Unfortunately, effective anti-tumor immunity does not occur to any significant level in most advanced-stage disease. This failure of the host to raise an immune defense is attributable to insufficient and/or ineffective immune stimulation. Normally, activation of the immune response is triggered by activating dedicated antigen-presenting cells that in turn are activated by the presence of foreign antigens. The stimulation of antigen presenting cells induces an orchestrated series of events involving natural killer cells, T helper and cytotoxic T cells, macrophages, and B cells, as well as the production and secretion of multiple cytokines, antibodies, chemokines and colony stimulating factors.

The present invention maximizes the powerful potential of the initiator of the immune cascade, the "foreign" antigen. Rather than depend on the tumor-associated and/or tumor-specific antigens to act as the initiator or priming antigen, a priming antigen is supplied, the cascade is initiated and the immune response to the antigens associated with the tumor is amplified accordingly. This approach exploits and amplifies the normal host immune mechanisms in vivo because the engineered cancer cells that will prime a strong response and deliver the molecules that define the specificity. Such cells can be advantageously engineered from autologous cancer cells, type cells obtained from cell lines or from human tissue from patients with the same type of cancer. The disclosed methods are effective in generating an immune response to a specific cancer without toxicity to normal cells. The treatment is not only selective but appears to be long-term and has promise as a prophylactic vaccine in subjects at risk for development of a specific cancer.

While many other cancer vaccines utilize immunopotentiators such as protein, bacterial, viral, chemical or naked DNA adjuvants, which can evoke an immune response, that response is not necessarily directed toward tumor cells and certainly not to subpopulations of tumor cells expressing minor antigenic variants. Only by genetically altering heterogeneous tumor cells to express priming antigens in accordance with the present invention, can the strength of the immune system be brought to bear specifically where it is needed. The disclosed approach not only favors a specific immune response, it is much less likely to evoke an adverse autoimmune reaction, in part because it is a targeted response to abnormal cells.

More particularly, the present invention concerns methods for expressing highly immunogenic priming antigens in tumor cells, and using these modified cells for treating oncological diseases in mammals, particularly humans, but also including dogs, cats, and animals of agricultural significance such as cows, sheep chickens and turkeys. Highly immunogenic antigens may be selected from antigens that are recognized as conventional antigens, where recognition by T-cells involves both variable elements of the α- and β-chains of TCR in a normal immune fashion or from superantigens stimulate clonal proliferation of specific subsets of $V_\beta$ T-cells, particularly those families of regulatory proteins that can bind to the extracellular portion of an MHC molecule to form an "MHC:superantigen" complex that stimulates certain subsets of T-cells.

There are a number of polypeptides that prompt a strong immune response, including bacterial and some plant toxins.

Among the more commonly recognized toxins are the plant toxin ricin, *Pseudomonas diphtheria*, mouse mammary tumor virus Mtv-7, toxins of *Mycoplasma arthriditis*, *Staphylococcus aureus* endotoxins, B, C1, C2, C3, D, E and F, viral antigens such as those from rabies or herpes, endoparasitic antigens such as protozoan or helminth, Toxic Shock Syndrome Toxin and various retroviral antigens.

Antigens, such as Protein A, collagen adhesion protein and fibronectin-binding proteins from *S. aureus* as well as surface proteins of gram-positive bacteria may be employed. Others include fibronectin binding protein (F/SfbI), T antigen, serum opacity factor/SfbII, C5a peptidase, members of the Mga regulon and members of the M protein family including Class I and Class II Emm, Enn and Mrp, all from group A streptococci and other streptococci including group B, C and/or G; Cα, Rib and cβ from Group B streptococci; M protein, SzP, SeM and Protein G from group C and G streptococci; neuramimidase and β-N-Acetylhexoseaminindase which can be isolated from *Streptococcus pneumoniae*; various proteins such as antigen I/II (P1 protein, B antigen, Pac, IF, sr, SpaA), CshA, β-D-Fructosidase, various dextranases, sucrases, glucan-binding proteins and WapA (protein antigen III) from oral streptococci of the viridans group like *S. mutans*, *S. sobrinus*, *S. gordonii*, *S. sanguis* and *S. salivarius*; various types of fimbriae of *Actinomyces* strains such as *A. naeslundii* and *A. odontolyticus*; protein L and PAB from *Peptostreptococcus magnus*; aggregation substance (AS) isolated from *Entercoccus faecium*; CluA, N is P and PrtP from *Lactococcus* species; and members of the internalin family such as InlC2, InlCA, InlD and InlF from *Listeria* species.

In one embodiment, the invention includes methods for introducing a polynucleotide coding for a highly immunogenic priming antigen into a cell such as, for example, a tumor cell, so that the antigen is expressed by the transformed cells. Expression may be on the surface, internally, or, likely both internally and surface-expressed.

The invention therefore in one important aspect concerns novel methods for treating persons or animals afflicted with oncological disorders, or preventing oncological disorders in persons or animals predisposed to such oncological disorders, such as solid tumors, soft tissue tumors, leukemias, lymphomas and their various metastases and micro metastases. The method comprises providing a patient in need of treatment for an oncological disorder with cells, such as tumor cells that have been transformed to express an antigenic protein.

In one embodiment, cells are treated so as to introduce a polynucleotide encoding a highly antigenic protein that will be expressed by the cells, and then providing a patient in need of such treatment with the transformed cells of the invention. In a preferred embodiment, the antigen is an M-like protein, such as Emm55, or a fragment or variant thereof. The expression of full length and truncated versions of the Emm55 protein in a cell are specifically exemplified.

The invention also concerns methods for treating or preventing oncological disease in a mammal that comprises modifying a cell to express a first highly immunogenic antigen in a cell, and optionally further modifying the cell to express a second antigenic polypeptide and providing the mammal with the transformed cells. In one embodiment, the subject method comprises expressing an antigen, such as Emm55 protein, and a foreign MHC antigen, such as a class II antigen, in a cell and providing a subject in need thereof with the transformed cells that express antigen and foreign class II MHC antigen. In another embodiment, the method comprises expressing an immunogenic antigen such as Emm55 or a functional variant thereof and a cytokine on a cell surface and providing the subject with the transformed cells expressing the antigen and cytokine.

A further embodiment comprises expressing an immunogenic antigen, a foreign MHC antigen and a cytokine in a transformed cell and providing a patient with the transformed cell. Appropriate cytokines include interleukins, such as IL-1, IL-2, IL-3, IL-4, IL-12, TNFα, IFNα, IFNβ, IFNγ, GM-CSF, MIP1β, MIP1α, TGFβ and other suitable cytokines capable of modulating immune response. The expressed cytokines can be either retained on the cell surface or secreted by the cell. The antigen may be an antigen alone or an antigen complex, such as those from pigs (Sykes et al., 1991) or *Mycobacterium* (EP 6571 68), or any antigen that has been shown to be highly immunogenic. Generally speaking, a highly immunogenic antigen can be characterized as inducing an acute immune response in a xenotransplant.

The methods of the invention can he used in combination with other therapies that are useful in treating cancer. These include, for example, surgical resection of the tumor, radiotherapy, chemotherapy, and antibody directed anti-tumor therapy, such as tumor-specific antibodies conjugated with toxins. Also contemplated for use in conjunction with the subject invention are other cancer therapies, such as dendritic cell cancer vaccines (Banchereau and Steinman, 1998; Gilboa, et al., 1998).

It is believed that any of a number of highly immunogenic proteins that can be expressed in a selected cancer cell will provide a useful vaccine. As an example of a particular embodiment, the protein EmmL 55, or Emm55, was employed to modify a neuroblastoma tumor cell. The resulting Emm55 cancer cell vaccine has succeeded where other vaccines based on stimulatory molecules have failed. Emm55 was chosen because it is a highly antigenic protein and is one of the few bacterial antigens that have been expressed on the surface of a mammalian cell. Emm55 is not toxic to mammalian cells, as shown experimentally in mice where it does not produce unwanted side effects. Additionally, Emm55 does not appear to be rheumatogenic. Emm55 was initially chosen as a model antigen because it is a common antigen and reintroduction in humans is expected to elicit a rapid and increased anamnestic response, which in turn will have a significant additional therapeutic effect. In contrast to some so-called superantigens, Emm55 does not produce an overblown immune response in a non-immune fashion so that the immune response to Emm55 does not result in clearance of the immune effectors before a therapeutic effect is realized. Thus, selection of an appropriate priming antigen includes consideration of whether or not too strong an immunological response will be generated.

As discussed, a number of other priming antigens can be used, and are best first identified as "priming" antigens, then selected on the basis of availability of the encoding gene. The emm55 gene for example is readily available; however, other foreign genes such as MHC genes, such as MHC class I, II and DR genes, and/or genes encoding cytokines can be inserted and expressed in the cell transformed to express the antigen and optionally used in combination with each other.

Optionally, tumor cells expressing a priming antigen can be irradiated prior to administration. Previous studies have shown that boiling and freeze-thaw loading techniques failed to generate protective immunity (Strome et al., 2002), whereas irradiated cells seem to retain immunogenicity (Soiffer et al., 1998). Irradiation produces cells that are viable but unable to replicate, two important characteristics.

Genes encoding other immunogenic proteins and/or functional variants of the encoded proteins and a gene encoding a foreign class II MHC can be introduced into and expressed in a tumor cell. Polynucleotide molecules encoding highly immunogenic antigens are preferably used to transform cells in vitro. Polynucleotides encoding appropriate antigens and, optionally, MHC class II can he introduced into tumor cells using standard techniques known in the art, such as electroporation, targeted liposomes, viral and retroviral vectors and transfection with naked DNA. The modified cells can then be introduced into a cancer patient; for example, directly into the tumor from which the cells were modified or, in leukemia, the modified leukemia cells can be introduced directly into the bloodstream.

As used herein the term "foreign MHC antigen" refers to MHC antigens that are distinct from the MHC antigens naturally expressed on the cells of the person or animal. MHC antigens within the scope of the invention include class I, class II and class III antigens. Alternatively, foreign antigens, whether MHC antigens or not, may be referred to as "heterologous."

Of course, selected cancer cells could be transformed in vivo; however, in order to be effective it is believed that specific targeting modes would have to be associated with the transforming or infecting means. In vivo transformations can be accomplished using any of a variety of methods well-known in the art, such as using targeted liposomes, viral vectors, and direct injection with naked DNA via numerous methods, but it is believed that ex vivo methods may be more effective for non-solid tumors like leukemias while in vivo methods may be preferable for solid tumors.

The invention also concerns a cell or population of cells transformed with a polynucleotide molecule or molecules encoding an antigen, such as a bacterial antigen, and, optionally, a foreign MHC antigen, such as class II antigen, and/or a cytokine. In a preferred embodiment, the polynucleotide encodes an Emm55 polypeptide, or a fragment or variant thereof. Particularly preferred are truncated versions of M-like proteins exemplified herein.

The materials and methods of the present invention can also he employed in combination with cytokine or other immunomodulating therapies. Also contemplated within the scope of the methods of the present invention are cells transformed with other streptococcal antigens that are expressed in the cell in conjunction with foreign class II MHC expression. Particularly highly immunogenic streptococcal antigens include those from groups A, D and B. Other immunogenic antigens may also be employed, including staphylococcal endotoxins B, C1, C2, C3, D, E, F, *Mycoplasma arthriditis* toxins, *Shigella* toxins, *Pseudomonas diphtheria* antigens and mouse mammary tumor MTV-7 toxin.

The invention also includes truncated immunogenic proteins, and in particular the polynucleotides that encode truncated proteins that exhibit higher activities or higher cell-surface expression compared to the full-length parent polypeptide when expressed in transformed cells. In a preferred embodiment, a truncated Emm55 protein comprises the sequence encoded by the emm55 gene where the protein coding region starts at the second in-frame ATG codon at 761 bp (SEQ ID NO. 2) in the nucleotide sequence of the emm55 gene. The resulting 375 bp deletion at the 5' end of the gene resulted in an absence of around 125 amino acids at the N-terminus, which means the mature protein has been shortened by 84 amino acids but maintains the wall sorting signal, the PGTS-rich domain, the wall associated region, the C repeats, the membrane anchor and polar tail. A truncated version of Emm55 protein can be produced using the plasmid pSVK3/emm55 described herein.

Highly immunogenic antigens, disparate MHC antigen, and cytokine proteins that can be used in the present invention include not only those isolated proteins having the same amino acid sequence as found in nature, including allelic variants, but also those variant proteins having mutations such as conservative amino acid substitutions, additions and deletions in the protein sequence, as long as the variant protein retains biological or immunotherapeutic activity.

Oncological disorders that can be treated using the methods and compositions of the present invention include lymphomas; leukemias; carcinomas of the bladder, breast, lung, cervix, colon, kidney, liver, ovary, prostate, pancreas, cartilage, testis, tongue, uterus and thyroid; sarcomas such as those of the pelvis, rhabdomyo (muscle), bone and osteogenic, brain tumors; gliomas; gliobastomas; neuroblastomas; melanoma; hepatomas; medulloblastoma; and Wilm's Tumors.

As is well known in the art, the amino acid sequence of a protein is determined by the nucleotide sequence of the DNA. Because of the redundancy of the genetic code, a single amino acid can be coded for by more than one coding nucleotide triplet (codon). Accordingly, different nucleotide sequences can code for a particular amino acid sequence. The amino acid sequences of the proteins of the subject invention can be prepared by nucleotide sequences other than the wild-type or native sequences. Functionally equivalent nucleotide sequences encoding the amino acid sequence of these proteins and fragments thereof can be prepared by known synthetic procedures. Accordingly, the invention includes use of such functionally equivalent nucleotide sequences.

Thus, the scope of the subject invention includes not only specific nucleotide sequences exemplified herein, but also all equivalent nucleotide sequences coding for proteins of the invention having substantially the same antigenic, immunogenic, or therapeutic activity.

BRIEF DESCRIPTION OF THE DRAWINGS

FIG. 4 shows a comparison of expected and actual sequences of the pSVK3/emm55 construct. Line one, SEQ ID NO:1, is the expected consensus sequence of the junction of the pSVK3 vector and the 5' end of the amplified nucleotide sequence containing the emm55 gene; line two, SEQ ID NO:2, represents the actual sequence of the pSVK3-emm55 junction; and line three, SEQ ID NO:3, is the confirmation of a suspected mutation. Except for this single mutation in the sequence at the site of the first start codon which shifted the transcription start site to the second ATG codon at 761 by position of the emm55 gene causing the expression of a truncated recombinant protein, the analyzed gene exhibited the typical sequence of emm55.

FIG. 6A shows the normal growth characteristics of untransfected Neuro-2a cells, exemplified by the formation of a monolayer.

FIG. 6B shows Neuro-2a transfected with MHC II (pcDV 1/α and pcDV 1/β). Neuro-2a cells which have been transfected with pcDV 1/α and pcDV 1/β, no longer form the characteristic monolayer of untransfected Neuro-2a cells as seen in FIG. 6A. Instead, after transfection, the cells began to grow in clumps. This new growth characteristic indicates a substantial alteration in the surface of the cells affecting their ability to adhere to plastic and to each other.

FIG. 6C shows Neuro-2a transfected with truncated emm55 (pSVK3/emm55). Neuro-2a cells which have been transfected with pSVK3/emm55, no longer form the characteristic monolayer of untransfected Neuro-2a cells as seen in FIG. 6A. Instead, after transfection, the cells began to grow in clumps. This new growth characteristic indicates a substantial alteration in the surface of the cells affecting their ability to adhere to plastic and to each other.

FIG. 6D shows Neuro-2a transfected with emm55 (pcDNA3/emm55) Neuro-2a cells which have been transfected with pcDNA3/emm55, no longer form the characteristic monolayer of untransfected Neuro-2a cells as seen in FIG. 6A. Instead, after transfection, the cells began to grow in clumps. This new growth characteristic indicates a substantial alteration in the surface of the cells affecting their ability to adhere to plastic and to each other.

BRIEF DESCRIPTION OF THE SEQUENCES

Figure 1:
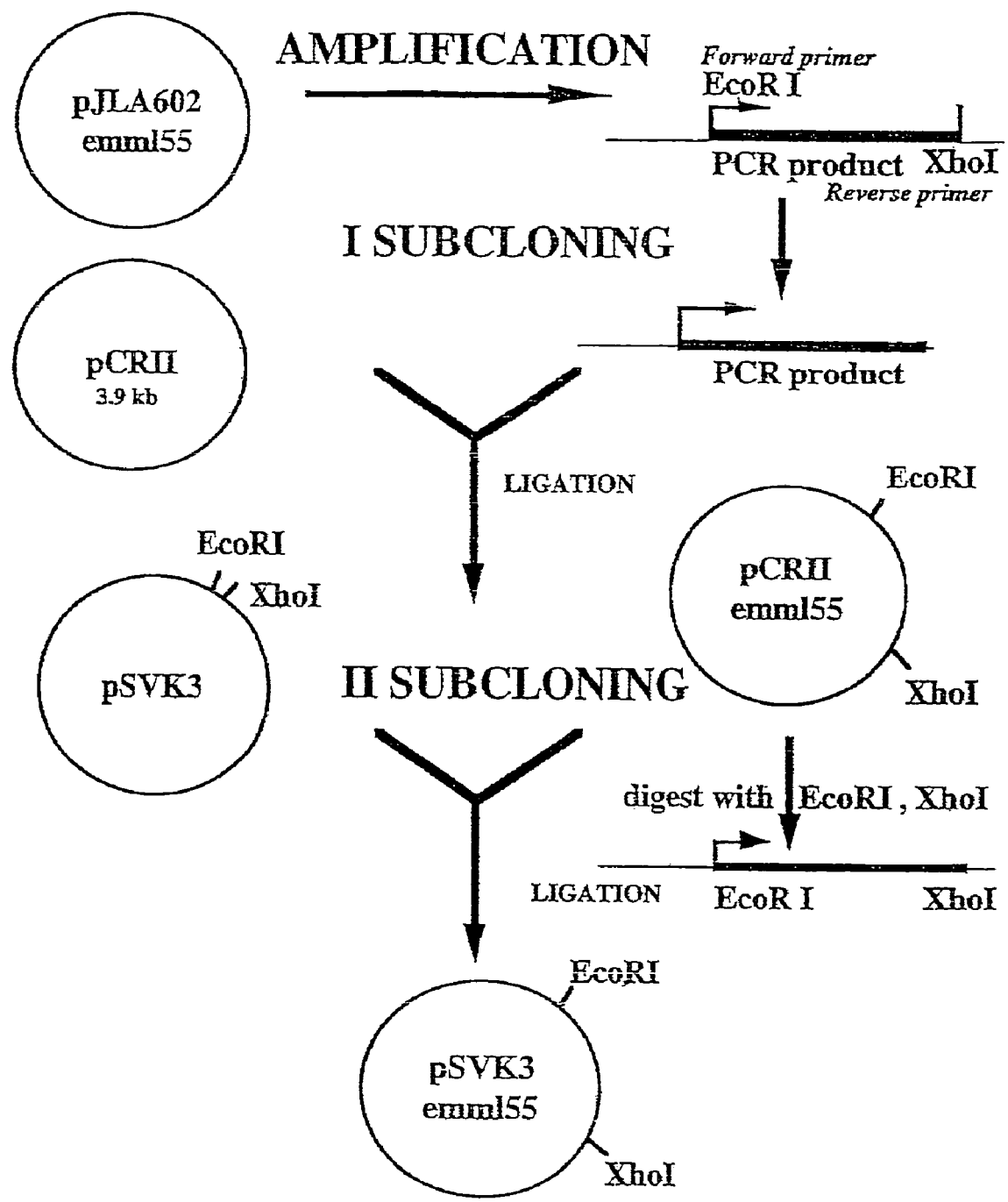
FIG. 1 shows construction of the pSVK3/emm55 expression vector. The emml55 (emm55) gene was amplified by PCR from the pJLA 602 vector using the primers shown in Table 1. The amplified fragment was subcloned into the pCR II vector. The emm55 gene was subsequently excised from pCR II with Eco RI and Xho I and further subcloned into the pSVK3 expression vector.

SEQ ID NO. 1 shows the nucleotide sequence of a pSVK3/emm55 construct according to the invention.

SEQ ID NO. 2 shows the nucleotide sequence of a truncated pSVK3/emm55 construct according to the invention.

SEQ ID NO. 3 shows the partial nucleotide sequence of pSVK3/emmL, 55 construct according to the invention.

SEQ ID NO. 4 shows an oligonucleotide primer used to amplify an emm55 gene according to the invention.

SEQ ID NO. 5 shows an oligonucleotide primer used to amplify an emm55 gene according to the invention.

SEQ ID NO. 6 shows an oligonucleotide primer used to sequence an emm55 gene according to the invention.

DETAILED DESCRIPTION OF THE INVENTION

Cancer

During the transformation process, malignant neoplasms grow into a disorganized mass, however, they usually retain some resemblance to the normal tissue from which they arise. Upon histological examination, tumors can be classified according to cell type origin. For example, tumors of epithelial origin are classed as carcinomas. Sarcomas arise from tissues of mesodermal origin. Carcinomas and sarcomas can be further distinguished as adenocarcinomas, hepatocarcinomas, osteosarcomas or fibrosarcomas. Other types of cancers include leukemias and various types of tumors of primitive origin such as neuroblastoma and meduloblastoma. Malignant cancers can affect humans as well as many animal species.

It is well understood that the main reason all cancer cells are not removed from the body is because these cells are seen by the immune system as "self"; i.e., they are the host's own cells, and because they are poorly immunogenic. The goal of the present invention was to develop a new type of cancer vaccine by showing that the introduction of a bacterial gene into a human cancer cell would make the cancer more readily detected by the immune system. The tumor cells were modified to express a highly immunogenic bacterial polypeptide, causing invasive tumor cells infecting the body to be rejected by the immune response of the host.

In order to develop immunotherapies for the treatment of cancer, the different ways parasitic tumor cells might manage to evade the immune system was first considered, particularly by studying how these abnormal cells develop. Although each tumor probably begins by the clonal reproduction of a single cell, additional changes eventually give rise to a heterogeneous mixture of different subclones. One way to look at these subclones is that they are in effect antigenic variants. Once under the selective pressure of the host's immune response, low antigenic variants gain advantage over subclones that express fewer or more immunogenic molecules. The less immunogenic and the lower the density of the tumor-associated antigens on the plasma membrane, the more likely the tumor cells will fall below the threshold of immune detection and become invisible to host surveillance.

Tumor antigens are subject to antigenic modulation, i.e., the tumor antigens appear to be temporarily lost after exposure to specific antibodies, although alternatively, tumors may simply suppress the activities of immune effector cells such as T-cells and macrophages. On the other hand, a few isolated tumor cells may contain too few antigens to stimulate an effective immune response so that by the time immunity has developed, the tumor is beyond the capability of the immune system to destroy it. Some tumors may even interfere with normal immune responses by invading lymphoid tissues or secreting immunosuppressive factors.

While tumor-specific protein or peptide vaccines are by definition specific for a particular tumor, a major concern in their use is tumor heterogeneity. Although tumor cell clones expressing the tumor-specific peptide epitopes may be destroyed, clones that do not express the epitope escape immune attack. As discussed, tumors are not clonal but are comprised of an amazing diversity of cells. The inventors reasoned that whole tumor cells would serve as more effective vaccines, i.e., such a vaccine would not only include a cross-section of tumor cells, but each tumor cell itself would carry its own complete complement of tumor antigens. This means that tumor cell variants, such as radio- or chemo-resistant variants, would be specifically targeted by the immune response primed by the "foreign" antigen.

With this in mind, a new cancer cell vaccine was developed with the objective of stimulating a strong and selective immune response in vivo against cancer cells, but not normal, healthy cells.

Success in using the new cellular vaccine was demonstrated in a murine model system. Expression of a highly immunogenic (priming) antigen in a neuroblastoma cell prevented or drastically reduced tumor development with no observable metastasis. Out of 72 mice inoculated with tumor cells that expressed the priming antigen, only two mice developed tumors, and after several days, these tumors regressed completely. This is in contrast to 67 of the 72 mice inoculated with unmodified tumor cells, which developed tumors, see Table 4.

Figure 9:
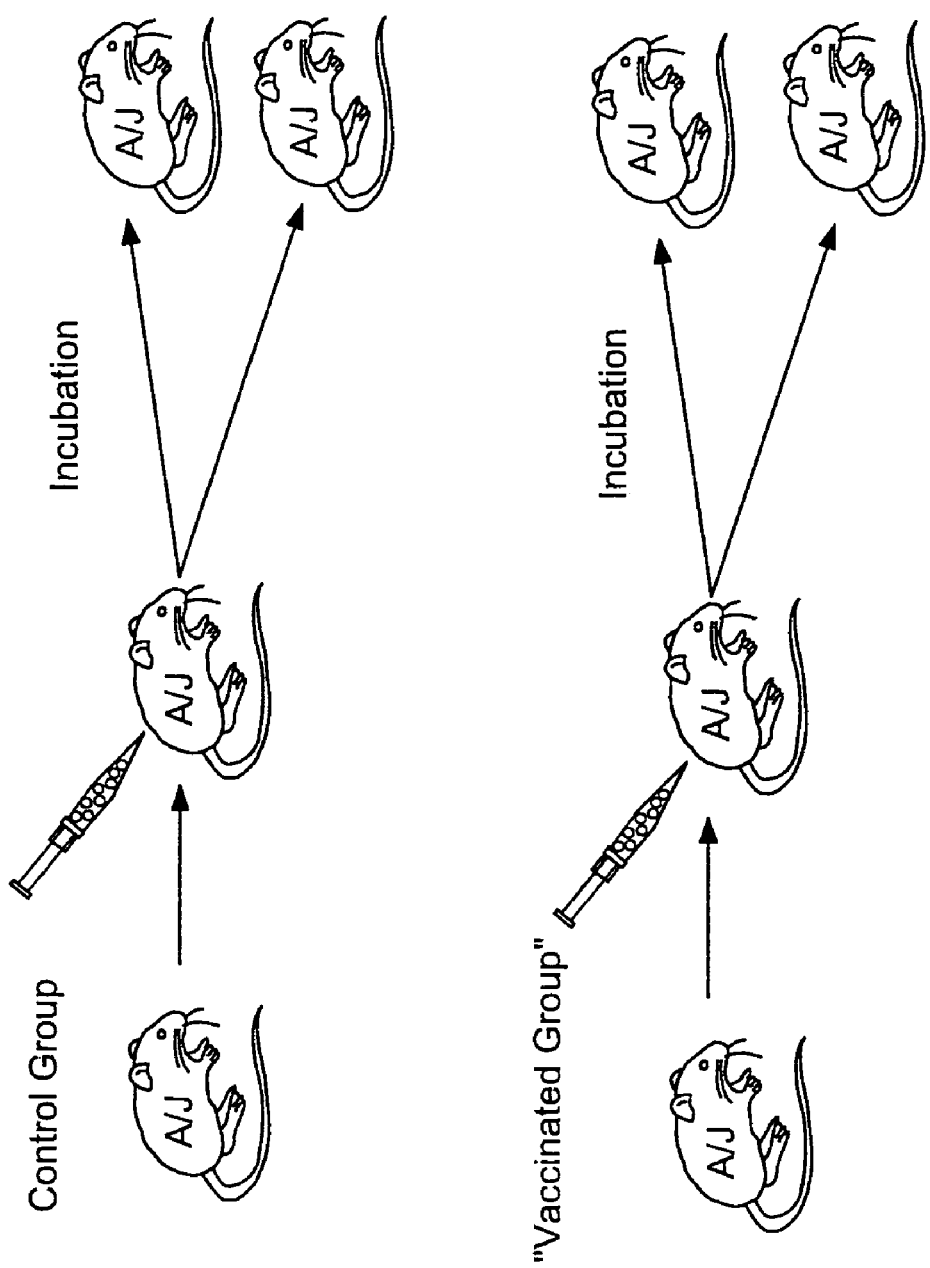
FIG. 9 shows the inhibition of tumor growth in mice pre-immunized with Neuro-2a cells expressing Emm55. Thirty-six mice vaccinated with either $3 \times 10^6$ or $1 \times 10^6$ Neuro-2a cells expressing Emm55, were subjected to challenge with $3 \times 10^6$ untransfected Neuro-2a cells. Of these, 8 eventually formed tumors, but 2 of these tumors regressed completely. Of the 18 mice which were inoculated with $3 \times 10^6$ Neuro-2a cells (N-2-a) without prior vaccination, 17 developed tumors.
Figure 10:
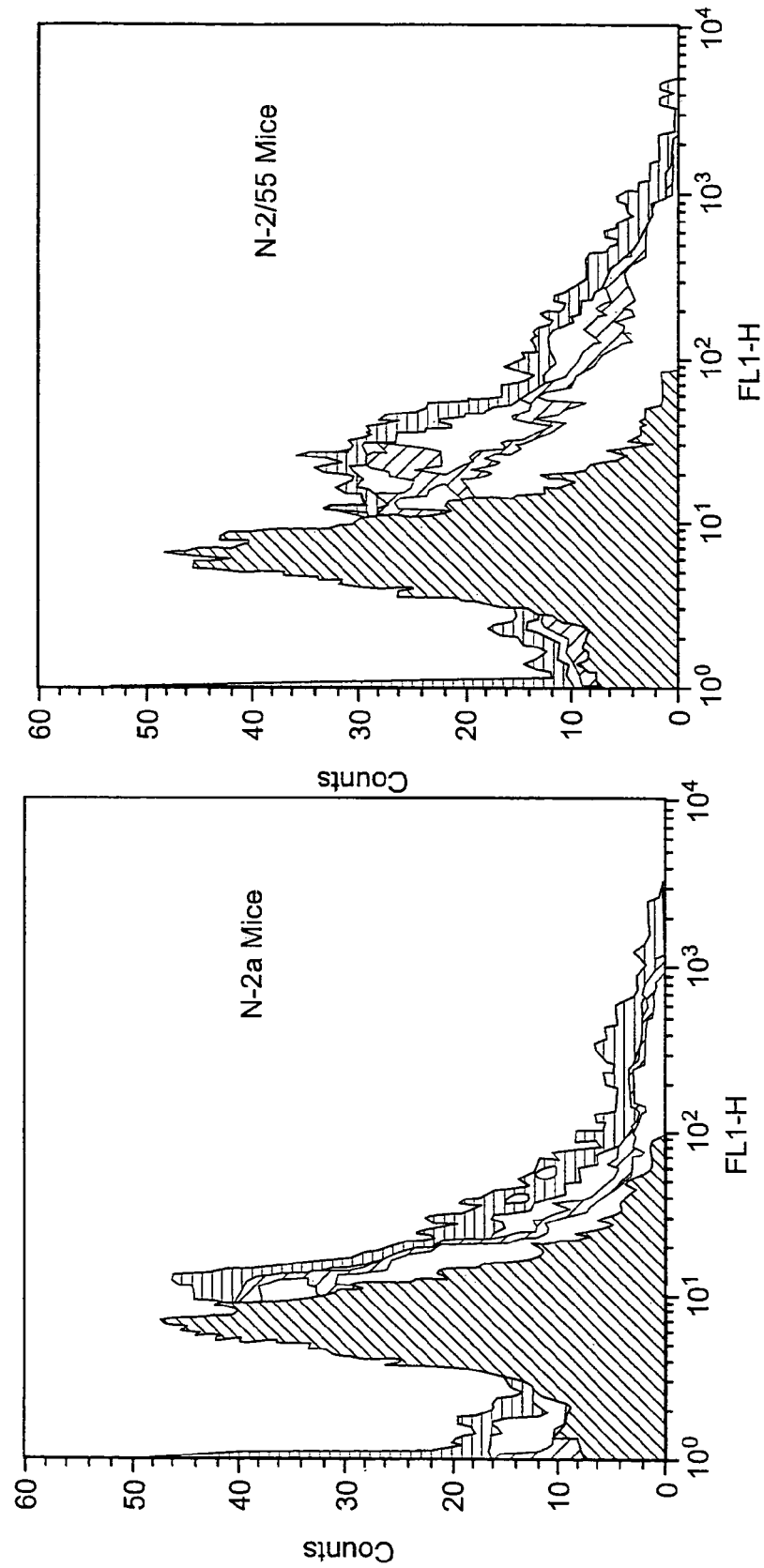
FIG. 10 compares the ability of sera from mice pre-immunized with Emm55-expressing Neuro-2a cells (N-2/55 Mice) with sera from mice inoculated with unmodified Neuro-2a (N-2a Mice) to bind Neuro-2a cells. The sera from mice inoculated with Neuro-2a cells (left panel) is far less reactive to Neuro-2a cells than the sera from mice immunized with Neuro-2a/Emm55 (right panel). This indicates that a heightened immune response specific for Neuro-2a antigens was primed by the presence of Emm55.

Even more surprising, was the observation that mice inoculated with tumor cells expressing the priming antigen were protected from challenge with unmodified tumor cells, see Table 5. In this experiment, of the 8 of 36 mice that eventually developed tumors, tumor development was 3 times slower in 4 of the mice and the size of the tumors only reached half the size of the controls; tumor onset was delayed over 7 fold in 2 others, and in 2 mice the tumors completely regressed (FIG. 9). The priming antigen initiated an increased immune response specific to the tumor cells as evidenced by the presence of anti-tumor cell antibodies in the sera of individual mice (FIG. 10).

The striking protection provided by the modified neuroblastoma cells is expected with other highly immunogenic antigens expressed in virtually any cancer cell. The surprising results in the neuroblastoma system are possible because an in vivo response was elicited, which recognizes the modified cancer cells as foreign or non-self. Thus, even where an immune system is comprised, it is likely that the body will generate at least some response to the foreign cells.

Neuroblastoma was a convenient choice as a first test cancer because the well-established mouse cancer cell, Neuro-2a, is recognized as mimicking the disease in humans. It is an especially aggressive tumor that can develop from small numbers of cells and will consistently kill its host within 2 weeks of onset if left untreated. The aggressive characteristics of Neuro-2a in S/J mice make any improvement in its prognosis highly significant. Another characteristic of this model is that Neuro-2a grows as a heterogeneous population of cells, a characteristic it shares with human neuroblastoma tumors. The remarkable results in the murine model provide a high expectation of parallel results in humans, supported additionally by the acceptance of cancer mouse models as bellweathers in human disease treatments.

The marshalling of such an effective immune response to the neuroblastoma tumors indicates that similar modifications to other types of cancer cells will provide cancer cell vaccines and effective immunotherapies. All tumor cells by definition are mutated and therefore are inherently different from their normal counterparts which are seen as "self" by the immune system. To become tumors in the first place, tumor cells are adept at avoiding clearance by immune surveillance mechanisms, yet the present invention shows conclusively that it is possible to intervene by priming the immune system to counterattack.

For this reason, regardless of whether the cancer is a leukemia, a lymphoma, a sarcoma, a carcinoma or any other type of malignancy, because cancers are made up of cells and are amenable through genetic modification to expressing the priming antigen, any type of cancer is amenable to participating in the development of its own vaccine.

The resulting cascade ending in clearance of the cancer cells by immune effector mechanisms can be initiated by an antigen that is highly immunogenic, yet which is not cleared by the innate arm of the immune response before a specific immune response can be generated. Because it is believed that the priming mechanism is displayed on the surface of the tumor cells to some degree, the avoidance mechanisms upon which tumor cells normally depend are thwarted. In the same manner, the priming mechanism to generate an immune response is not dependent on the tumor cell which expresses it. The tumor cell need only to maintain tumor cell identity to be recognized by the immune response.

Any cancer cell may be used with the disclosed method. Sources include the host or other mammalian sources. The cells can be modified with polynucleotide molecules encoding highly immunogenic antigens (e.g., Staphylococcal or Streptococcal), foreign MHC antigens and/or cytokines using standard techniques known in the art. Cells are preferably transformed ex vivo for in vivo use. When cancer cells are modified ex vivo, according to the invention, they can be reinfused into the mammal. The encoding polynucleotides can be delivered to the cells using, for example, targeted liposomes that harbor the polynucleotide molecules. Viral vectors, such as adenovirus, adeno-associated virus, retrovirus, pox virus, herpes virus, plasmids and nucleic acid, can also he used for transforming cells with the polynucleotide molecules encoding the selected highly antigenic polypeptides useful in the practice of the present invention. Cells can also be transfected using naked DNA, i.e., transfection by direct injection of a tumor with naked DNA encoding proteins useful in the subject methods.

Vaccines

The present invention contemplates the disclosed cancer cell vaccines for use in both active and passive immunization. Immunogenic compositions, useful as vaccines, may be prepared most readily from immunogenic peptides and a select cancer cell. The cancer cell will be from host cancer cells or from the same type of cancer cells, which may be obtained from appropriate cell lines or from non-autologous tumor cells. Ideally, the cancer cells are taken from the host; however, it is contemplated that cancer cell vaccines can still be employed when autologous cells cannot be obtained. In such a case, vaccines prepared from cell lines or non-autologous donors can be administered.

The cancer cell vaccines of the present invention are best prepared ex vivo by transforming representative cells of the selected cancer with one or more of the described highly immunogenic antigens. Transformation methods are well-known and can be used to insert an appropriate expression vector into a cell; e.g., by transfection, infection or electroporation. However, for in vivo administration, the formulation may be a preparation of an expression vector, which contains the gene encoding the priming antigen. Administration of this type of formulation would be directly into the tumor via needle and syringe, gold particles and ballistic guns (gene guns), liposomes and or by jet injection techniques.

Once formulated, the cancer cell vaccines will typically be prepared as injectables, in the form of suspensions. The cell suspensions may be mixed with excipients which are pharmaceutically acceptable and compatible with the cells. Suitable excipients include, for example, water, saline, dextrose, glycerol, ethanol or the like and combinations thereof. In addition, if desired, the vaccine may contain minor amounts of auxiliary substances such as wetting or emulsifying agents, pH buffering agents, or adjuvants that enhance the effectiveness of the vaccine.

Vaccines are conventionally administered parenterally, by injection, for example, either subcutaneously or intramuscularly and are administered in a manner compatible with the dosage formulation, and in such amount as will be therapeutically effective and immunogenic. Alternatively, intradermal injection of the vaccine may be preferable. The quantity to be administered depends on the subject to be treated, including, e.g., the capacity of the host's immune system to synthesize antibodies, and the degree of protection desired. Precise amounts of the transformed cells required will depend to some extent on the judgment of the practitioner and the age, health, sex, etc., of the host. However, suitable dose ranges may be determined from animal models and initial clinical studies. Generally, it is contemplated that on the order of $10^6$ transformed cells will be required.

It is not believed that adjuvants will be required except perhaps in cases where the host immune system is weakened or compromised. Adjuvants commonly used include agents such as aluminum hydroxide or phosphate (alum), admixture with synthetic polymers of sugars (Carbopol RTM), aggregation of protein in the vaccine by heat treatment (e.g. 70-101° C.) Aggregation by reactivating with pepsin treated (Fab) antibodies to albumin, mixture with bacterial cells such as C. parvum or endotoxins or lipopolysaccharide components of Gram-negative bacteria, emulsion in physiologically acceptable vegetable oils vehicles such as mannide mono-oleate (Aracel A) or emulsion with a 20% solution of perfluorocarbon (Fluosol-DA.RTM) used as a block substitute may also be employed.

In certain instances, it will be desirable to administer multiple doses of the vaccine, usually not exceeding six vaccinations, more usually not exceeding four and preferably one or more, usually two or three. The vaccinations will normally be at from two to twelve week intervals, more usually from three to five weeks. Periodic boosters at intervals of 1-5 years, usually three years, may be required to maintain a protective level of antibodies and memory T cells.

Pharmaceutical Compositions

Pharmaceutical compositions containing the cancer cell vaccine are preferably administered parenterally, intraperitoneally, intradermally or intramuscularly. Pharmaceutical forms suitable for injection include sterile aqueous solutions or dispersions for extemporaneous preparation of the solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin, by the maintenance of the required particle size in case of a dispersion and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Upon formulation, solutions will be administered in a manner compatible with the dosage formulation and in such amount as is therapeutically effective. The formulations are easily administered in a variety of dosage forms preferably as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intradermal and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Materials and Methods

VECTORS. The pSDVI and pSVK3 vectors are useful for expression studies in a wide variety of mammalian cell lines. They contain sequences for efficient replication in $E.\ coli$, an mRNA splice site and polyadenylation signal from SV40 for replication and expression in eukaryotic cell line. The genes for Dwl4α and β currently reside separately on pSDV1, a mammalian expression vector originally designed by Okayama and Berg (1987). These plasmids must be cotransfected in order for the MHC class II-DR4 antigen to be expressed on the cell surface. The use of these constructs acts as a positive control in the transfection and expression in Neuro-2a cells and in the suppression of tumor growth.

Emm55 Expression Vector. Production of an expression vector expressing the emm55 gene is based on the amplification of the emm55 gene by PCR and generation of restriction sites at the ends of the product, which allows subsequent ligation to the multiple cloning site of the pSVK3 expression vector. Briefly, the resulting PCR fragment was gel-purified and subcloned into the pCRII vector. Restriction mapping confirmed that several clones contained the correctly amplified product. A single clone was used for further study. The restriction endonucleases Hind III and EcoRI were used to excise the PCR product from the pCRII cloning vector, gel-purified, and subcloned into pSVK3.

Amplification of emm55 by the Polymerase Chain Reaction (PCR): The cDNA for emm55 was isolated from the parental vector, pJLA 602, which was kindly provided by Dr. M. Boyle, (Medical College of Ohio, 3000 Arlington Avenue, P.O. Box 10008, Toledo, Ohio 43699). PCR assays were carried out in a 50 µl format for product preparation using the thermocycler Twin Block System (Ericomp, San Diego, Calif.). Each PCR reaction contained the following final concentration of reactants: 100 ng template DNA; 2.5 units Taq-Polymerase (Promega, Madison, Wis.); 1 mM of each primer (Oligo, Wilsonville, Greg.); 1.75 mM $MgCl_2$ (Promega, Madison, Wis.); 5 µl of 10×PCR buffer (Promega, Madison, Wis.). and 250 mM dNTPs (Pharmacia Biotech, Piscataway, N.Y.).

For cloning purposes, the primers contained 5' tags with either an EcoRI or XhoI restriction site. The primers used to amplify the emm55 gene and for sequencing the amplified gene products are listed in Table 1. Each assay was overlaid with 50 µl of mineral oil and denatured for 5 min at 94° C. The reaction mixture was subjected to 35 cycles of 1 min at 94° C. followed by 1 min at 60° C., 1 min at 72° C. and 10 min at 72° C. PCR products for cloning were combined and concentrated using a Microcon Concentrator-100 (Amicon, Beverly, Mass.).

The combined products were then applied to 1% (w/v) agarose gel and separated by electrophoresis at 50 V for 150 min. The resulting 1.6 kb product representing the amplified emm55 gene was extracted from the gel and purified by QIAquick Column (Qiagen, Chatsworth, Calif.). The DNA was precipitated by incubating 0.1 volumes of 3 M sodium acetate with 2.5 volume of ethanol at 70° C. for 2 hours followed by centrifugation at 12,000×g for 15 min. Finally, the DNA was resuspended in TE buffer (10 mM Tris, HCl and 1 mM EDTA, pH 8.0) and the yield was analyzed by electrophoresis prior to ligation. Electrophoretic analysis of the PCR yield was performed by applying 4 and 8 µl of the product directly onto a 1% (w/v) agarose gel and compared with the DNA Mass Ladder from Gibco (Grand Island, N.Y.).

TABLE 1

List of Oligonucleotides for amplification and sequencing of emm55

| Oligo-nucleotide | | Sequence 5' to 3" | to target site |
|---|---|---|---|
| (a) Oligonucleotides for amplification of emm55 coding sequence | | | |
| AS1 | TAG AAT TCA TGG CTA AAA ATA CCA CGA ATA G | (SEQ ID NO:4) | 5' end of emm55 |
| AS2 | TTC TCG AGT TAG TTT TCT TCT TTG CGT TTG AC | (SEQ ID NO:5) | 3' end of emm55 |
| (b) Oligonucleotide utilized for sequencing the amplified emm55 produce | | | |
| AS3 | CAG TTC CGC CCA TTC TTC | (SEQ ID NO:6) | 5' portion of pSVK 3/emm55 |

Cloning of emm55 Gene into the pCRII Vector: The TA cloning kit (Invitrogen, San Diego, Calif.) uses the pCRII vector and provides a quick, one-step cloning strategy for the direct insertion of a PCR product into a plasmid vector. TA cloning works by using a Taq polymerase nontemplate-dependent activity, which adds a single deoxyadenosine (A) to the 3' ends of PCR products and by using the pCRII, a linearized vector which has 3' deoxythymidine ('1') residues, allowing efficient ligation.

The amount of PCR product needed to ligate with 50 ng (20 fmoles) of pCRII vector was estimated using the formula below:

$$X_{ng} PCR\ product = \frac{(Y_{bp}\ product)(50\ ng\ pCRII\ vector)}{(Size\ in\ bp\ of\ the\ pCRII\ vector = 3900)}$$

Two ligation reactions using the following final concentrations were set up:

1) for 1:1 (vector:product) reaction, 50 ng of pCRII vector:20.51 ng of emm55 DNA were used;

2) for 1:3 reaction, 50 ng of pCRII vector:61.53 ng of emm55 DNA were used.

One µl of 10× ligation buffer, T4 DNA ligase (4.0 Weiss units) and H$_2$O up to 10 µl final volume were used for each ligation reaction. Ligation reactions were incubated overnight at 14° C. and used for transformation of competent One Shot INVαF' E. coli cells, provided in the One Shot competent cell kit.

Construction and Analysis of the pCRII/emm55. In order to subclone the emm55 gene into pSVK3, emm55 was amplified from the parental vector, pJLA 602 and restriction sites necessary for subcloning were added to the ends of the amplified product. Agarose gel electrophoresis of the emm55 PCR product showed that the size of amplified gene was 1.6 kb and the amount of the amplified product was 8 ng per 1 µl of the TE buffer.

One Shot INFVαF' E. coli. competent bacterial cells were then transformed with pCR II/emm55. Bacterial clones were screened for the presence of the recombinant construct by white/blue selection. One clone showed the expected size 5.5 kb and was chosen for restriction analysis. The pCR II/emm55 construct, when digested with Eco RI and, Xho I restriction enzymes, released the emm55 gene. Agarose gel electrophoresis of the digested product show the expected band pattern, 1.6 kb for emm55 and 3.9 kb for the pCRII vector. The amplified emm55 gene was used for further cloning into the pSVK3 expression vector.

Transformation of One Shot INVαF' E. coli Competent Cells: Two µl of 0.5 M (β-mercaptoethanol (β-ME) were added to 50 µl of One Shot INVαF' competent cells and mixed directly with 2 µl of each ligation reaction, incubated on ice for 30 m in. and heat shocked at 42° C. for 30 sec. After transformation, the bacterial cells were grown in 450 µl of SOC medium (2% w/v tryptone, 0.5% w/v yeast extract, 10 mM NaCl, 2.5 mM KCl, 10 mM MgC$_2$, 10 mM MgSO$_4$, and 20 mM glucose) at 37° C. for 1 hour with vigorous shaking. Fifty µl and 200 µl from each transformation vial were spread on Luria-Bertani (LB), (10 g bactotryptone, 5 g bacto yeast extract, 10 g NaCl, for 1 liter, pH 7) agar plates containing 50 µg/ml of ampicillin and 40 µg/ml X-Gal and incubated overnight. After incubation, plates were shifted to 4° C. for 24 hours to allow proper color development.

Restriction Analysis of pCRII/emm55: Restriction analysis was used to determine the presence and orientation of the emm55 insert. Blue-white screening of bacterial clones was performed in order to obtain the clones containing the amplified insert. White colonies were used for cracking gel analysis. Briefly, cells from white colonies were transferred into 5 ml of LB broth supplemented with 50 µg/ml ampicillin and grown overnight aerobically at 37° C. Five hundred µl of bacterial culture were transferred into microcentrifuge tubes and centrifuged for 1 min at 1500×g. Bacterial pellets were lysed in cracking huffer (1% w/v SDS, 2 mM EDTA, 0.4 M sucrose, 0.05 M Tris HCl and 0.01% (w/v) Bromophenol Blue) and bacterial lysates were run on a 1%, (w/v) agarose gel. Clones which had a 5.5 kb size plasmid were used for further analysis. Preparation of the DNA for restriction analysis from One Shot INVαF' cells was then performed using standard procedures. The bacterial cells were lysed using the technique and the DNA purified by phenol/chloroform extraction (Sambrook et al., 1989). The recombinant DNA was subsequently digested with the following restriction endonucleases: Eco RI (12 units/µl), Xho I (10 units/µl) in combination (Promega, Madison, Wis.).

Subcloning of emm55 into pSVK 3: To clone emm55 into the pSVK 3 plasmid (Pharmacia, Piscataway, N.Y.), emm55 cDNA was excised from the pCRII emm55 construct by Eco RI (12 units/µl) and Xho I (10 units/µl) (Promega, Madison, Wis.) (FIG. 1). The digestion was carried out overnight at 37° C. The sample was run on a 1% (w/v) agarose gel at 50

V for 180 min and the 1.6 kb band was then extracted from the gel and purified using a gel extraction kit (Qiagen, Chatsworth, Calif.) according to the instructions of the supplier. The pSVK3 plasmid (Pharmacia Biotech, Piscataway, N.Y.) was digested with Eco RI (12 units/µl) and Xho I (10 units/µl) in order to produce compatible ends needed for ligation with emm55. Restriction enzymes were inactivated by incubation at 70° C. for 20 min. The amount of emm55 cDNA needed to ligate with 50 ng of pSVK 3 vector (3919 hp) was estimated using Formula I. Three ligation reactions were set up using the following final concentrations, for 1:1 (vector:insert) reaction 50 ng:20.41 ng, for 1:3, 50 ng:61.24 ng and for 1:6, 50 ng:122.48 ng of pSVK 3:emm55 cDNA, 1 µl of 10× ligation buffer, T4 DNA ligase (4.0 Weiss units) and H$_2$O up to 10 µl final volume for each ligation reaction.

Figure 3:
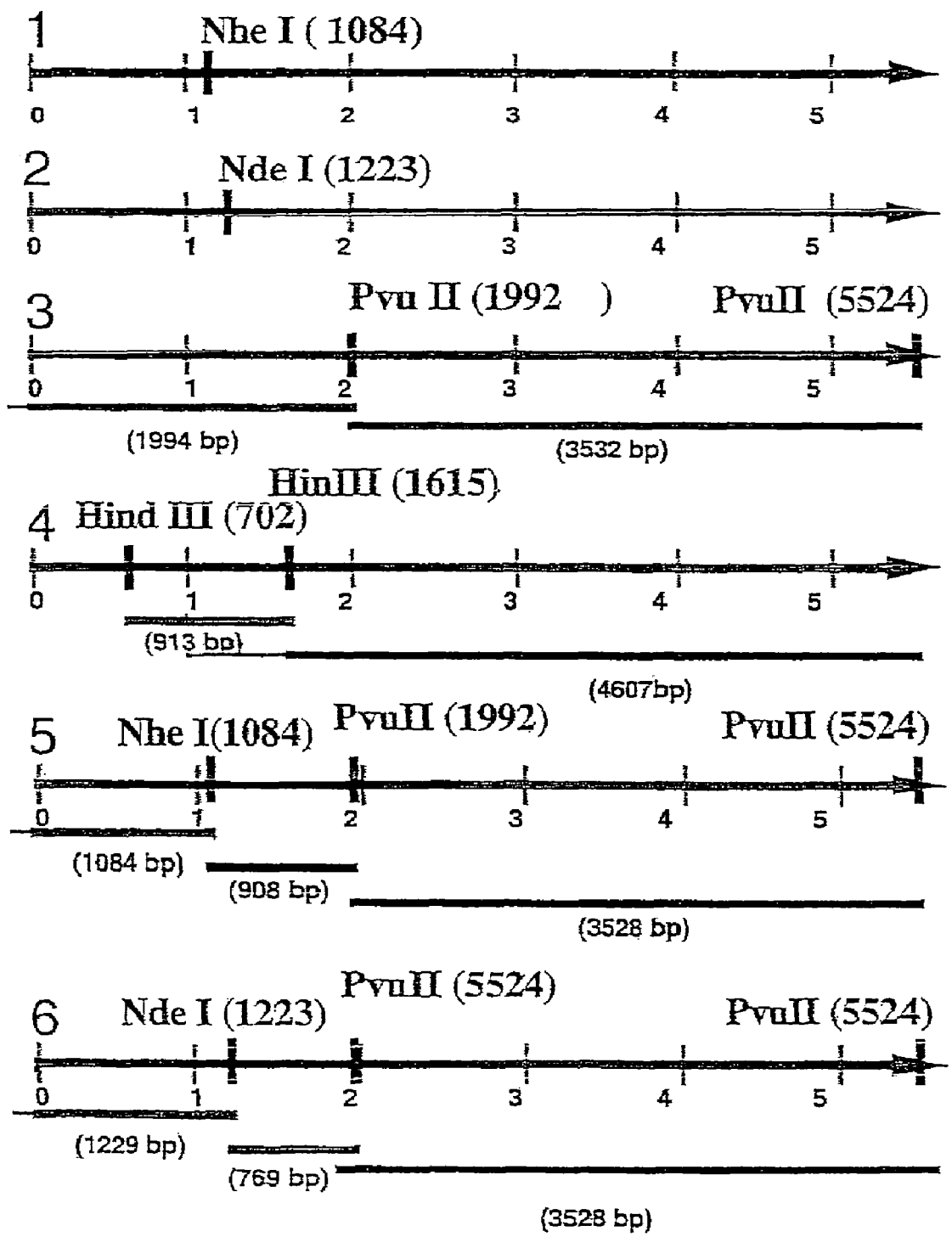
FIG. 3 shows a restriction map of the pSVK3/emm55. The map confirmed the presence and orientation of the emm55 insert. The 5.5 kb recombinant pSVK3/emm55 plasmid was linearized with Nhe I as expected. Digestion with Pvu II yielded a 2 kb and a 3.5 kb band and digestion with Hind III generated two band, 0.9 kb and 4.6 kb. Double digestion with Pvu II and Nhe I resulted in three bands of approximately 1 kb, 2 kb and 5.5 kb and digestion with Pvu II and Nde I generated three bands, 0.77 kb, 1.2 kb and 3.5 kb.

Construction and Analysis of pSVK3/emm55. From the 20 analyzed bacterial clones, transformed with the pSVK3/emm55, four clones with 5.5 kb size were selected and digested with restriction enzymes. Three out of four clones transformed with pSVK3/emm55 exhibited the expected banding pattern and one was used for the subsequent analysis. pSVK3/emm55 when digested with Nhe I and with Nde I generated a 5.5 band as expected. Digestion with Pvu II yielded a 2 kb and a 3.5 kb band and digestion with Hind III generated two bands, 0.9 kb and 4.6 kb. Double digestion with Pvu II and Nhe I resulted in three bands of approximately 1 kb, 2 kb and 5.5 kb pairs and digestion with Pvu II and Nde I generated three bands, 0.77 kb, 1.2 kb, and 3.5 kb (FIG. 3). Restriction analysis of pSVK3/emm55 revealed that the recombinant construct had the expected size (5.5 kb) and the expected map.

In order to confirm that the correct product was amplified, sequence analysis was performed. The partial sequence of the emm55 gene and the pSVK3 vector was determined and is presented in FIG. 4. FIG. 4 represents a comparison between SEQ ID NO:1, (top line) which is the expected consensus sequence of the junction of the pSVK3 vector and the 5' end of the amplified nucleotide sequence containing the emm55 gene; SEQ ID NO:2 (middle lane) which represents the actual sequence of the pSVK3-emm55 junction, and SEQ ID NO:3 (bottom line) which is a confirmation of a suspected mutation. Except for a single mutation in the sequence at the site of the first start codon which shifted the transcription start site to the second ATG codon at 761 by position of the emm55 gene causing the expression of a truncated recombinant protein, the analyzed gene exhibited the typical sequence of emm55 (FIG. 4). The second start codon is at 761 bp site of pSVK3/emm55.

Transformation of E. coli Cells. XL-1 Blue E. coli cells were transformed with the ligation products using a standard heat shock procedure. One hundred µl of ice-cold transformation buffer TMF (10 mM Tris-HCl, 50 mM CaCl$_2$, 10 mM MgSO$_4$×7 H$_2$O, filter sterilized) was added to 200 µl of XL-1 Blue E. coli cells and mixed directly with 2 µl of each ligation reaction, incubated on ice for 45 min. and heat shocked at 37° C. for 2 min. After transformation, the bacteria were left for 10 min at room temperature, then transferred into 500 µl of LB broth and incubated for 90 min at 37° C. Twenty five, 50, and 200 µl from each transformation culture were spread on to LB plates supplemented with ampicllin (50 µg/ml) and tetracycline (10 µg/ml) and then incubated overnight at 37° C.

Restriction Map of pSVK3/emm55 Construct: To determine the presence and orientation of the emm55 insert, bacterial colonies were isolated and grown overnight in LB broth with 50 µg/ml ampicillin. Four clones were chosen for plasmid isolation and restriction endonuclease analysis. The following endonucleases were used: Bam HI (10 units/µl); Nhe I (12 units/µl); Xho I (10 units/µl) and Eco RI (12 units/µl); Hpa I (10 units/µl) and Cla I (10 units/µl); Hpa I (10 units/µl) and Nhe I (12 units/µl). Clone number 2 was used for further map analysis. A restriction map was constructed using Nhe I (12 units/µl); Nde I (10 units/µl); Pvu II (10 units/µl); Hind III (10 units/µl); Pvu II (10 units/µl) and Nhe I (12 units/µl); Pvu II (10 units/µl) and Nde I (10 units/µl); and Eco RI (12 units/µl) and Xho I (10 units/µl).

Sequence Analysis of pSVK3/emm55: DNA sequence analysis was performed using pSVK3/emm55 as a template. Sequencing was carried out using a sequenase version 1.0 DNA sequencing kit (Amersham, Arlington Heights, Ill.), a C.B.S. SG-500-33 adjustable nucleic acid sequencer and the primers listed in Table 2 according to the Sanger method of dideoxy-mediated chain termination (Sanger et al., 1977). Denaturation of the double-stranded template was carried out by adding 0.1 volumes 2 M NaOH/2 mM EDTA and incubating 30 min at 37° C. The sample was neutralized by the addition of 0.1 volumes 3 M NaAc, pH 5.5, and the DNA was precipitated as above. The sample was redissolved in 7 µl distilled water. The annealing reaction was carried out by heating the DNA mixture (0.5 µg/µl) with the primers (1 mM) and 2 µl of the reaction buffer at 65° C. for 2 min. After incubation, the reaction was slowly cooled to 35° C. for 15-30 min. To the ice-cold annealed DNA, the following labeling reagents were added: 0.1 M DTT; 0.1 M, 2 µl diluted labeling mix; $^{35}$S dATP (0.5 µl); and Klenow sequencing polymerase (2 µl). The labeling reaction was carried out by incubating the reagents at room temperature for 2-5 min.

The reactions were terminated by adding the labeling reaction (3.5 µl) to the pre-warmed A, T, G, C termination mixtures (2.5 µl) and incubating at 37° C. for 5 min and quenched by adding 4 µl of stop solution. Before loading on a 6% (w/v) sequencing gel, the samples were heated for 2 min at 75° C. The gel was run at constant power of 35-40 W. After fixing the gel with 10% (w/v) methanol and 10% (w/v) acetic acid, the gel was transferred to 3 MM Whatman paper and placed under vacuum in a dryer for 40 min at 80° C. The gel was then exposed to X-ray film (Kodak) at room temperature for 24 hours and subsequently developed in a Kodak-M35A X-OMAT Processor.

Figure 2:
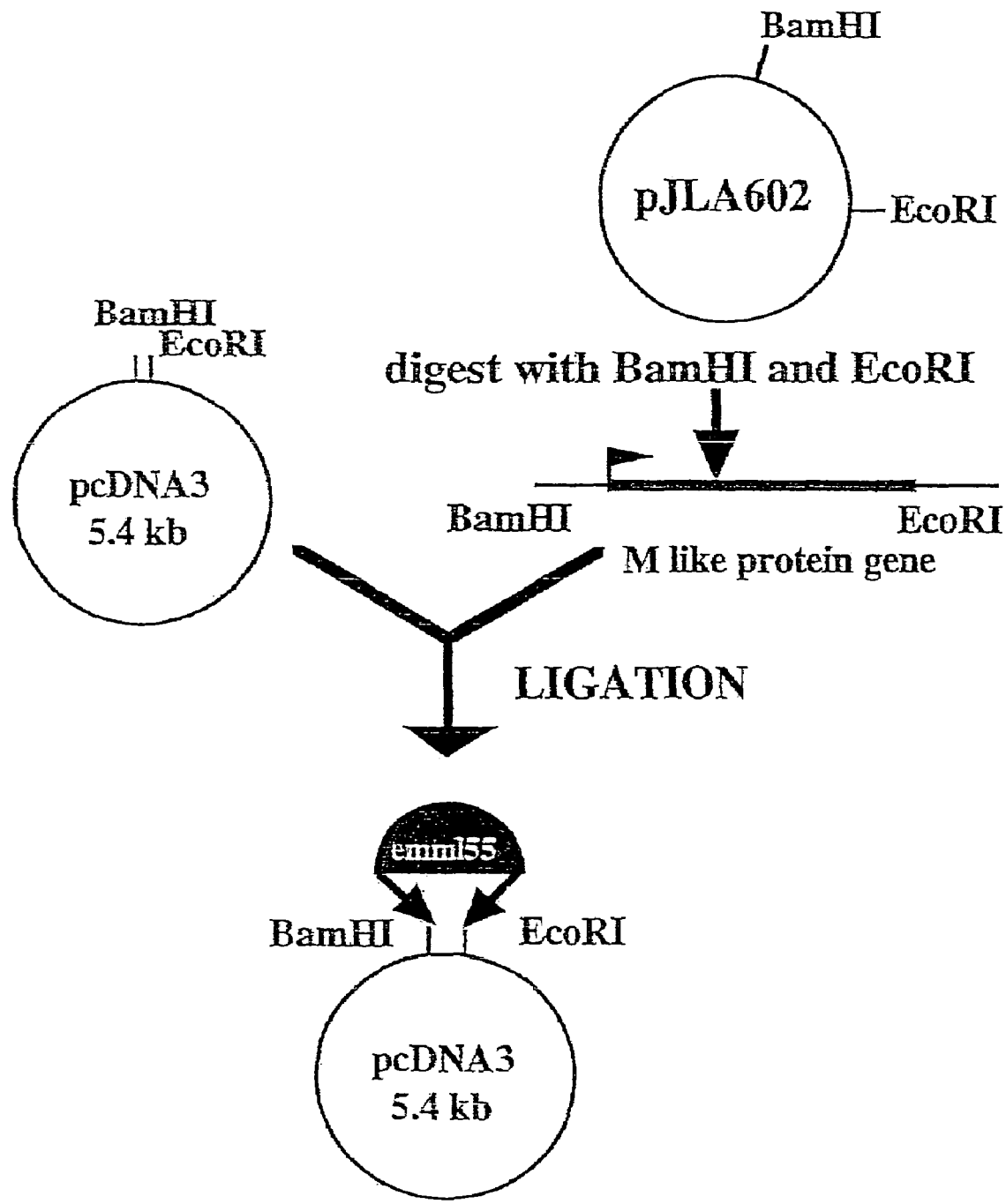
FIG. 2 shows construction of the pcDNA3/emm55 expression vector. A nucleotide fragment containing the emm55 gene was excised from pJLA 602 with Bam HI and Eco RI. It was subsequently ligated into the pcDNA3 expression vector to form pcDNA3/emm55.

Subcloning of emm55 cDNA into pcDNA3: The cDNA for emm55 was isolated from the parental vector, pJLA 602, which was kindly provided by Dr. M. Boyle. Isolation and preparation of the parental plasmid from E. coli DH5α was performed using standard techniques (Sambrook et al., 1989). The emm55 cDNA for was excised from the pJLA 602 by restriction endonuclease digestion with Bam HI (10 units/µl) and Eco RI (12 units/µl) (FIG. 2). DNA purification was by electrophoresis elution using a QIAquick gel extraction kit (Qiagen, Chatsworth, Calif.). The emm55 cDNA was ligated into the pcDNA3 expression vector (Invitrogen, San Diego, Calif.) which was prepared by double digestion with Bam HI (10 units/µl) and Eco RI (12 units/µl) as above, to reveal the necessary restriction sites.

Figure 5:
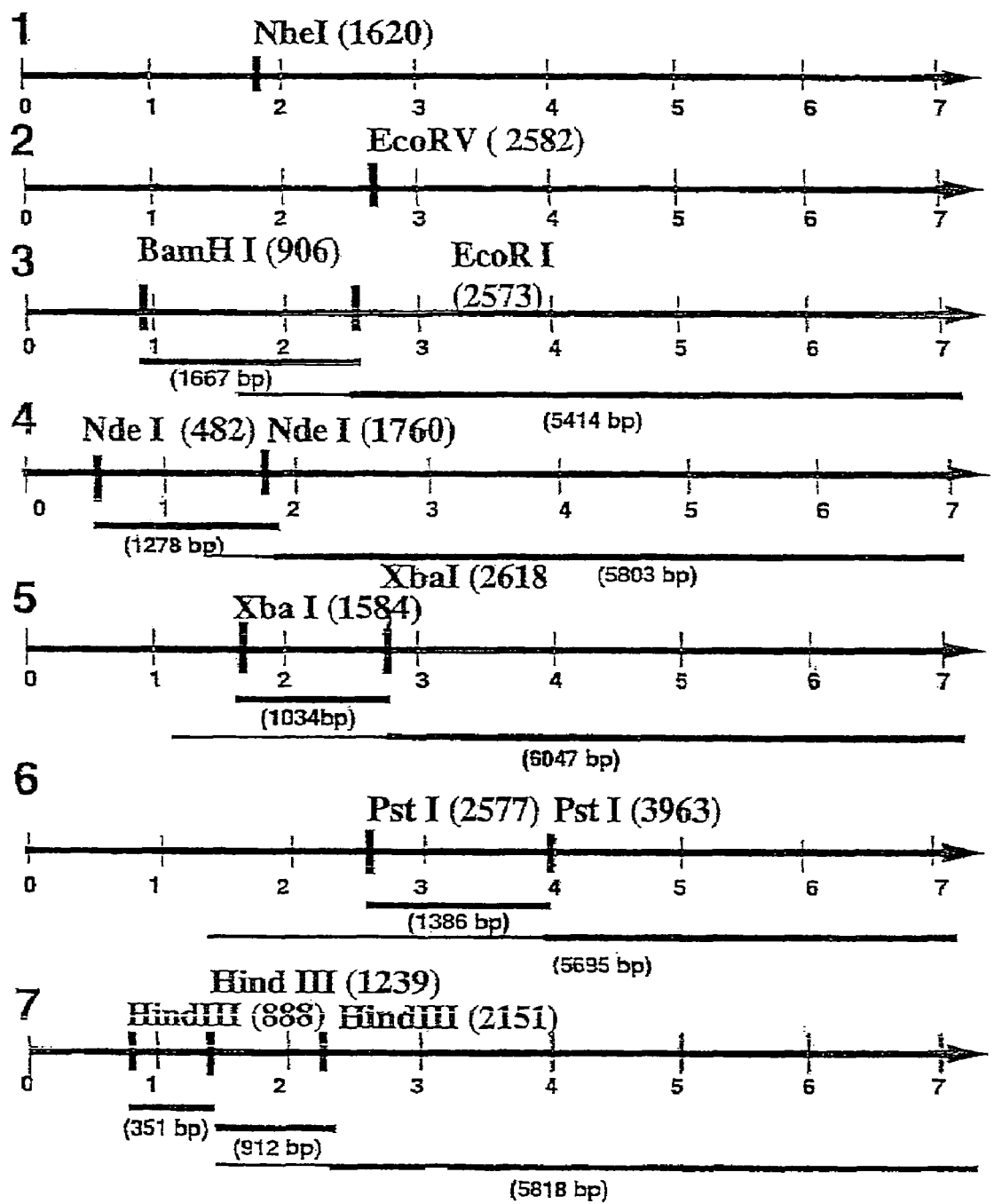
FIG. 5 shows a restriction map of the pcDNA3/emm55. The recombinant pcDNA3/emm55 plasmid was linearized by Eco RV, which recognizes a site in pcDNA 3 and by Nhe I which recognizes a site in emm55. Digestion with Bam HI and Eco RI yielded a 1.6 kb and a 5.4 kb fragment. Nde I recognizes sites in the vector and the emm55 gene, generating two bands (1.3 and 5.8 kb). There are two Pst I sites present in pcDNA 3 and this enzyme generated the expected two fragments (1.4 kb and 5.7 kb). Hind III generates three bands, 351 bp, 912 bp and 5818 bp. The restriction digest of the pcDNA3-emm55 construct and agarose gel electorphoresis confirm the identity of this plasmid.
Figure 6A:
FIGS. 6A-6D show morphology of untransfected or transfected Neuro-2a cells.
Figure 6B:
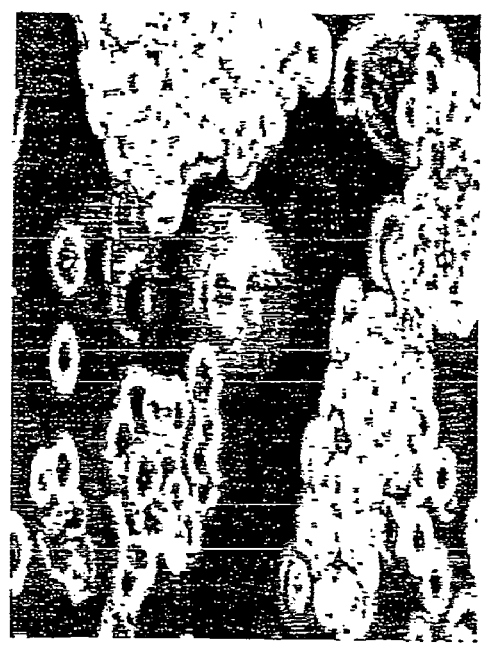
Figure 6C:
Figure 6D:

Construction and Analysis of the pcDNA 3/emm55. FIG. 5 shows results from the restriction analysis of pcDNA3/emm55. The digestion of three clones with Hind III and Pst I in separate reactions yielded the expected band sizes. One of these clones was analyzed by the subsequent restriction analysis. The recombinant plasmid was linearized by Eco RV, which recognizes a site in pcDNA3 and by Nhe I, which recognizes a site in emm55. Digestion with Bam III and Eco RI yielded a 1.6 kb and a 5.4 kb fragment. Nde I recognizes a site the expression vector backbone and in the emm55 gene, generating two bands (1.3 kb and 5.8 kb). There are two Pst I sites present in pcDNA3 and restriction with this enzyme generated two fragments (1.4 kb and 5.7 kb). Hind III generates three bands 351 bp, 912 bp and 5818 bp. The restriction digests of the pcDNA3/emm55 construct and agarose gel electrophoresis confirm the identity of this plasmid. It was concluded that the recombinant plasmid could be used for the transfection of the Neuro-2a and other cell types.

E. coli JM109 high efficiency competent cells (Promega, Madison, Wis.) were transformed with the ligation reaction products, which were prepared as follows: The amount of emm55 cDNA was estimated using Formula I. Three ligation reactions were performed for 1:1 (vector:insert) 15.2 ng of emm55, for 1:3 45.6 ng of emm55, 5 ng of pcDNA 3 (5400 bp), T4 DNA ligase (4.0 Weiss units) and $H_2O$ up to 10 µl final volume for each ligation reaction. Reactions were incubated overnight at 14° C. and used for transformation of E. coli JM109 high efficiency competent cells. One hundred µl of bacterial cells were mixed with 2 µl of each ligation reaction. After gentle mixing, cells and DNA were incubated on ice for 2 min and transferred to 42° C. for 1 min. Cultures were then incubated in 1 µl LB broth for 45 min at 37° C. with shaking. Twenty, 50, and 200 µl of each culture were spread over the surface of LB agar plates supplemented with 50 µl/ml of ampicillin and incubated overnight. Cracking gel analysis was performed and three clones carrying 7,000 hp inserts were studied further.

Restriction Map of pcDNA3/emm55: Preparation of pcDNA3/emm55 DNA for restriction map analysis was performed by the mini-prep alkaline lysis method (Sambrook et al., 1989). Purified DNA from the three selected clones was analyzed by restriction endonuclease digestion with Pst I (10 units/µl), Hind III (10 units/µl) and Xba I (10 units/µl) and agarose gel electrophoresis. A single clone was chosen for the restriction map of pcDNA 3/emm55 and was digested with: Nbe I (12 units/µl); Eco RV (20 units/µl); Bam HI (10 units/µl) and Eco RI (12 units/µl); Nde I (10 units/µl); Xba I (10 units/µl); Pst I (10 units/µl); and Hind III (10 units/µl).

Statistics

Statistical Determination/Analysis: In vivo studies were designed to provide statistically significant evidence that any observed differences between treatment groups was a result of the manipulation and not due to other variations such as genetic differences or environmental factors. The appropriate number of mice per group was calculated to be 18. As stated by Dell et al. (ILAR Journal 43, 2002), in feasibility studies such as described herein, estimating the number of animals needed is usually based upon previous experience and/or guesswork. However, the data collected in the described experiments can be used in sample size calculations to determine the number of subjects that will be needed in designing drug protocols. The sample size employed was derived from a table for "Sample size for a four-group MANOVA" utilizing a power of 0.80 in anticipation of a very large effect.

The objective of the in vivo studies was to investigate the differences in tumorogenicity between control Neuro-2a tumor cells and a cancer vaccine prepared by genetically modifying tumor cells to express a selected immunogenic bacterial antigen, Emm55. The following experimental determinations were set up and used in the statistical analyses: (a) development of the tumor at the site of inoculation; (b) time required for the first measurable tumors to develop; (c) growth of the tumor during the study period; and, (d) growth rate of the tumor. The research design was to manipulate one independent variable, which was randomly assigned to groups. The statistical procedure used was a Multivariate Analysis of Variance.

Statistical power analysis was conducted to determine the sample size for each group. Statistical power analysis is a method for determining the likelihood that a particular test of statistical significance will lead to rejection of a false null hypothesis. The following factors were taken into consideration:

Sample size: power increases with sample size,

Level of significance: The second determinant of statistical power is the p value at which the null hypothesis is to be rejected. The research set the level of significance in this study to $p<0.05$, and Effect of size: This determinant of statistical power is an estimate of the magnitude of the difference, relationship, or effect in the population.

Following are examples that illustrate materials and procedures for practicing the invention. These examples are intended for illustrative purposes only and should not be construed as limiting.

EXAMPLES

In Vitro Studies

Example 1

Tumor cells. The tumor cells used in the in vitro transfection experiments and the in vivo studies were the murine neuroblastoma cell line, Neuro-2a. This cell line, a subclone of C1300 murine neuroblastoma, was obtained from the American Type Culture Collection (ATCC) and was deposited at the ATCC in May 1969 (ATCC CCL131). The parental cell line was maintained on Iscove's Modified Dulbecco's Medium (IMDM) supplemented with L-glutamine and 10% fetal bovine serum (FBS). The cells were routinely passaged once a week at a ratio of 1:4 in either 75 $cm^2$ or 150 $cm^2$ tissue culture flasks and maintained at 37° C. in a humidified atmosphere of 5% CO in air. In some cases the cultures were supplemented with penicillin (100 units/ml) and streptomycin (100 µg/ml).

Growth Curve of Neuro-2a Tumor Cells: Neuro-2a cells were harvested by trypsinization at 37° C. for 5 min. and centrifugation at 800×g for 10 min. at 25° C. Following enumeration by trypan blue exclusion, the cells were serially diluted ($6.4 \times 10^5$, $3.2 \times 10^5$, $1.6 \times 10^5$, $8 \times 10^4$, $4 \times 10^4$, $2 \times 10^4$, $1 \times 10^4$, $5 \times 10^5$, $2.5 \times 10^3$, and $1.2 \times 10^3$), plated in quadruplicate onto 96 well plates and incubated at 37° C., in a humidified atmosphere of 5% $CO_2$ in 95% air for 2, 4, 6, or 8 days. Cell proliferation was measured by the Alamar Blue assay (Alamar Bioscience, Sacramento, Calif.). This assay incorporates a fluorometric/colorimetric growth indicator which detects metabolic activity. This indicator both fluoresces and changes color in response to a chemical reduction of the growth media resulting from cell growth. Alamar Blue reagent was added aseptically to each well in an amount equal to 10% of the cell culture volume (20 µl) and incubated with for 3 hours under cell growth conditions. Absorbency was measured on a Ceres UV 900 HD (Bio Tek Instruments) at a wavelength of 570 nm. Background absorbance (600 nm) was subtracted prior to tabulating the data.

Cell proliferation assays were performed to estimate the growth characteristics of the Neuro-2a cells needed for subsequent experiment. Ten starting cell concentrations were continuously incubated over an 8-day period with cell numbers being determined every other day. Cell proliferation was measured using Alamar Blue. Results were expressed as a mean of Alamar Blue adsorbance of four cultures plus or minus standard error. The lower cell concentrations, up to $1 \times 10^4$ cells/ml, showed standard growth characteristics. In higher concentrations, between $2 \times 10^4$ and $4 \times 10^4$ cells/ml, cells grew exponentially for the first four days then reached stationary phase and started to die. Exponential growth was observed in concentrations between $8 \times 10^4$ and $1.6 \times 10^5$ cells/ml for the first two days and the viable count decreased slowly in the following days. Two cell concentrations: $2 \times 10^4$ and $1.6 \times 10^5$ cells/ml were chosen for use in for the drug sensitivity assay.

Drug Sensitivity Assay. A drug sensitivity assay was performed to establish the concentration of G418 needed for killing Neuro-2a cells. Cell death was measured by the Alamar Blue assay. The growth of Neuro-2a cells ($2 \times 10^4$ cells/ml) was efficiently suppressed by 500 μg/ml of G418. This concentration of the toxic agent caused growth inhibition of up to 78% after 2 days and the viability of cells dropped to zero after 6 days. Growth of Neuro-2a was also inhibited at concentrations of 400 and 300 μg/ml, while concentrations of 100 and 200 μg/ml of G418 had minimal effect on cell growth.

Inhibition Assay of Neuro-2a with G418: In order to determine the concentration of G418 (Gibco Laboratories, Grand Island, N.Y.) needed for selection of transfected cells, the following experiment was performed. Two cell concentrations ($2 \times 10^4$ and $1.6 \times 10^5$) were chosen and plated onto 96 well plates and G418 at five concentrations (100, 200, 300, 400, and 500 μg/ml) was added. All dilutions were plated in quadruplicate. Replicate plates were incubated at 37° C. in a humidified atmosphere of 5% $CO_2$ in air for 2, 4, 6, 8 or 10 days. Survival was assessed using the Alamar Blue assay.

Similar patterns of the growth inhibition by G418 were noted when cell concentration was $1.6 \times 10^5$ cells/ml. The most efficient inhibition of cell growth was observed when 500 μg/ml of drug was used. From these results it was concluded that 500 μg/ml is an effective amount of G418 for selecting stably transfected Neuro-2a cells.

Transformation of Neuro-2a Cells. In order to evaluate the expression on the cell surface of these antigens and to develop stably transfected Neuro-2a cell lines, i.e., Neuro-2a cells expressing both Emm55 and Dw14, Neuro-2a cells were electroporated with plasmids containing either the emm55 gene or the Dw14 α and β genes as described above. Expression of DW-14 and Emm55 proteins was analyzed by flow cytometry using monoclonal antibodies. Successfully transfected cells were sorted by FACS and evaluated over time. Within two hours of electroporation, greater than 80% of the Neuro-2a cells cotransfected with Dw14 α and β genes expressed MIHC class II-DR4 antigen on the surface. After 21 days, 50% of the cells still expressed this marker. Approximately 30% of cells transfected with the emm55 construct expressed detectable amounts of this antigen on their surface immediately following electroporation, but none was detected after 7 days. Sequence analysis revealed that the emm55 construct was missing the 5' ATG codon along with other 5' nucleotides. This presumably occurred during PCR amplification. Thus, it may be preferable to subclone the emm55 gene directly from the original plasmid into another expression vector containing a selectable marker as a means to keep selective pressure on the cells to retain the plasmid.

Transformation of Neuro-2a cells with pcDNA3/emm55, analysis of gene expression and selection of a stable line: Twenty μg of pcDNA3/emm55, linearized with Hind III, was electroporated into Neuro-2a cells at a concentration of $2 \times 10^6$ cells/ml at 260 V and 1050 μF. The cells were plated immediately in 5 ml IMDM and incubated at 37° C. in 5% $CO_2$ in air. After 48 hours, the media was withdrawn and replenished with media supplemented with G418 at 500 μg/ml. The cells were routinely passaged and maintained on IMDM supplemented with L-glutamine, 10% FBS and G418 (500 μg/ml).

For flow cytometric analysis, the transfected Neuro-2a cells were prepared by gently removing them from the tissue culture flasks with a sterile cell scraper. The cells were washed and collected by centrifugation at 800×g, resuspended in incomplete IMDM to concentration $1 \times 10^6$ cells/ml. The cells were then incubated for one hour with the primary antibodies at a dilution of 1:500 of antibody:cells. After washing, fluorescence of the antibody exposed cells was analyzed by an Epics Elite ESP (Coulter Electronics, Hialeah, Fla.). Anti-M-like protein antibody (polyclonal α II o and monoclonal 8 F-10; 25 C; and 15 (β3) were provided by Dr. M. Boyle (Boyle et al., 1994, and Boyle et al., 1995). After staining with primary antibody the cells were washed three times in incomplete medium then incubated in the presence of a Avidin FITC conjugate for polyclonal α II o or with mouse IgG-FITC (Becton Dickinson San Jose, Calif.) for the monoclonals at 1:1000 (secondary conjugate:cells) at 4° C. in the dark for 30 min. The exposed cells were washed three times, resuspended in a volume of 0.5 ml of incomplete IMDM then analyzed by flow cytometry. Immunoflourescence background was measured by comparing the staining of untransfected Neuro-2a with both the primary and secondary conjugate and secondary conjugate alone. In subsequent transfection experiments, the cells analyzed for expression of emm55 by flow cytometry were stained with a chicken polyclonal antibody specific to Emm55 and were permeabilized to allow for the staining of internal and external antigen present in the cells. The cells were analyzed using a Becton Dickinson FACSCalibur (FACSCAN) flow cytometer.

Gene Transfer of pcDV 1/α and pcDV 1/β into Neuro-2a by Electroporation

The MHC II cDNA (DR4, DW 14) expression vector, pCDV 1 (Okayama et al, 1987), was obtained from Peter K. Gregersen, (North Shore University Hospital, Cornell University Medical College, Manhasset, N.Y.). The plasmid constructs, pcDV 1/α and pcDV 1/β, were used for cotransfection of Neuro-2a cells with the MHC II, DR 4 gene. The α gene encodes the α domain of DW 14 and the β gene encodes for β domain of DW 14.

The cells were harvested and washed twice with incomplete IMDM. For each electroporation reaction, $2 \times 10^5$ ml of Neuro-2a cells was used. Cell suspension samples of 250 μl were mixed with 250 μl (0.1 μg/μl) each pcDV 1/α and pcDV 1/β DNA in a Gene Pulser Cuvette. The DNA samples were resuspended prior to mixing in 2× Hank's balanced salts buffer (Hbs) (1.4 mM $Na_2PO_4$, 10 mM KCl, 12 mM glucose, 275 mM NaCl and 40 mM HEPES, pH 7.2). Electroporation was carried out under three conditions: 1000 V, 21 μF; 450 V, 500 μF; and 300 V, 900 μF. After electroporation, the cells were placed on ice for 10 min then transferred to 6 well plates. The cells were incubated in complete IMDM at 37° C., under 5% $CO_2$. After 24 hours, 3 ml spent medium was replaced with 4 ml fresh medium and the cells were incubated for an additional 48 hours. Gene expression was measured by flow cytometry after 48 hours and after 18 days. For MHC II expression the primary antibody (anti-MHC DR-FITC) was purchased from Becton Dickinson (San Jose, Calif.). In order to obtain stably transfected cells, Neuro-2a cells were electroporated with 20 µg each of pSG1NEOpA, pcDV 1/α and pcDV 1/β at 260 V and 1050 µF. The cells were plated immediately in 5 ml of IMDM and incubated at 37° C. in 5% $CO_2$. After 48 hours, 3 ml spent medium was replaced with fresh 3 ml IMDM and G418 was added to final concentration of 500 G418 was replaced every five days.

Gene Transfer of pSVK3/emm55 into Neuro-2a by Electroporation pSVK3/emm 55 was transfected into Neuro-2a cells by electroporation. The Neuro-2a cells were prepared for gene transfer as previously described except that the number of cells used for each reaction was $2 \times 10^6$/ml. pSVK3/emm55 was linearized before transfection with Bam HI (10 units/µl). Twenty µg DNA was resuspended in $H_2O$ and used for each electroporation reaction. Electroporation was carried under three different conditions: 220V, 1050, µF; 260 V, 1050 µF; and 300 V, 1050 µF. Following electroporation, the cells were plated on the 9 wells culture plates and 5 ml of complete IMDM was added. Gene expression was measured by flow cytometry after 72 hours and 11 days. In order to obtain stably transfected cells, Neuro-2a cells were electroporated with 20 µg each of pSGINEOpA and pSVK3/emmL 55 at 260 V and 1050 µF. Cells were cultured under conditions as described for gene transfer of pcDV 1/α and pcDV 1/β.

Morphological Characteristics of Stable Transfected Cell Lines Introduction of the vectors into cells changed the cell morphology (FIG. 6). The transfected cells selected by G418 (panels B, C, and D) grew in characteristic clumps, whereas the untransfected neuroblastoma cells formed an even monolayer (panel A). This finding cannot he explained by the presence of G418 in the medium since in previous experiments (inhibition assay) Neuro-2a did not show any morphological changes in the presence of drug.

Expression of MHC Class II Antigen by Neuro-2a Cells. Using flow cytometry, it was found that the recombinant antigen, DR 4, DW 14 (MHC II) was successfully expressed by Neuro-2a cells. Forty-eight hours after electroporation, up to 84.8% of the cells were able to express the recombinant antigen. The expression of the DR 4, DW14 antigen was still present 18 days after electroporation. Twenty nine to 48.2% of the Neuro-2a cells were able to bind mAbs against DR 4, DW 14 after 18 days.

The level of DR 4 expression was dependent on the electroporation conditions. In a second independent experiment, up to 55.1% of Neuro-2a cells were able to express the recombinant antigen 48 hours after electroporation (Table 2). The highest level of fluorescence was observed in cells transfected at 1000 V and 21 µF. Fifty three % of cells expressed MHC II-DR 4 antigen when they were electroporated at 50 V., 500, µF and 33.2% of cells expressed the antigen when they were transfected at 300 V and 900 µF.

TABLE 2

Expression of MHC II-DR 4 and pSVK3/Emm55 by Neuro-2a cells

| | Electroporation conditions | | | | | |
|---|---|---|---|---|---|---|
| | 220 V 1050 µF | 260 V 1050 µF | 300 V 1050 µF | 300 V 900 µF | 450 V 500 µF | 1000 V 21 µF |
| Expression of MHC II-DR4 | NA | NA | NA | 33.2% | 53.2% | 55.1% |
| Expression of pSVK3/EmmL55 | 7% | 35% | 20.4% | NA | NA | NA |

Expression of Truncated emm55 Gene in Neuro-2a Cells. Flow cytometry was used to determine the efficiency of transfection of Neuro-2a cells with the pSVK3/emm55 construct. The cells demonstrated moderate expression of the truncated emm55 gene (Table 2). Seventy two hours after transfection, 35% of the cells exhibited immunofluorescence using polyclonal antibodies when electroporated at 260 V and 1050 µF, 20.4% at 300 V and 1050 µF. and 7% at 220 V and 1050 µF. Eleven percent of Neuro-2a cells were able to express the recombinant protein 11 days after electroporation.

Figure 7A:
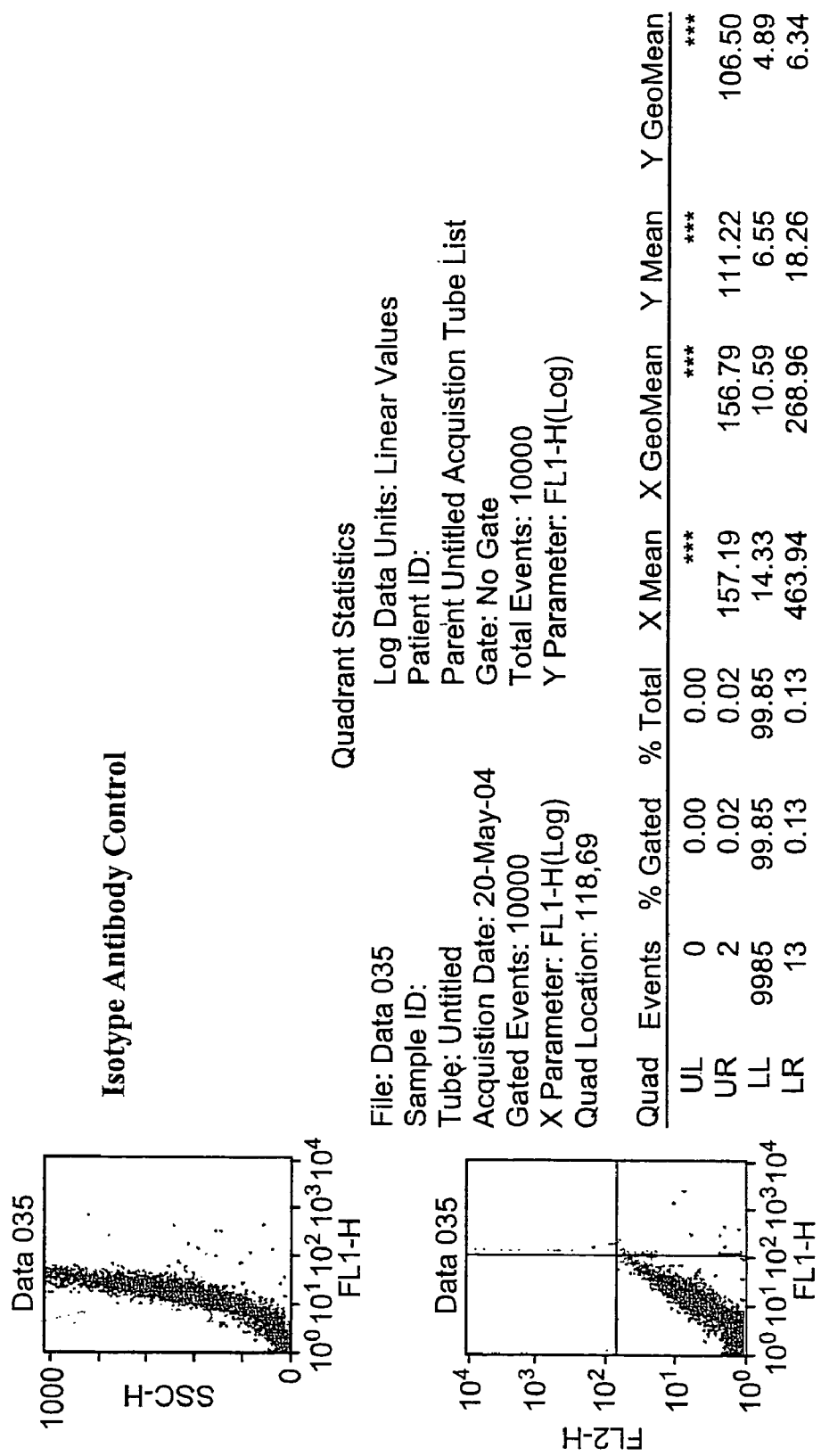
FIG. 7 represents the flow cytometric analysis showing Emm55 protein expression in emm55-transfected neuroblastoma cells. The top panel shows the isotype control binding to the emm55-transfected neuroblastoma cells. The bottom panel shows the binding of the anti-Emm55 monoclonal antibody (25-C3) to emm55-transfected neuroblastoma cells as evidenced by the shift in fluorescence from the lower left quadrant of the plot to the lower right quadrant. Approximately 90% of the cells were recognized by the 25-C3 monoclonal.
Figure 7B:
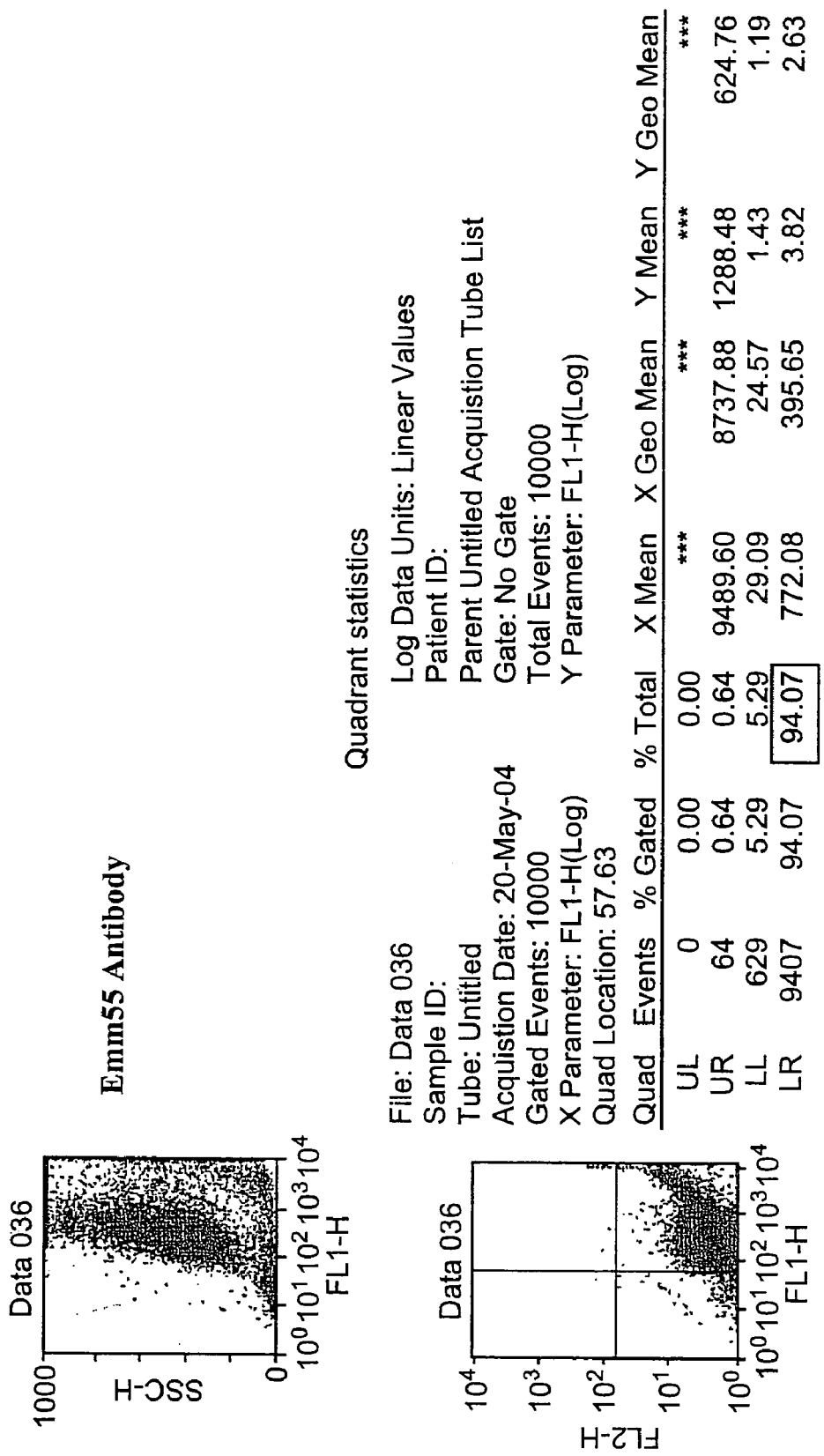

Stable Expression of Full length emm55, Truncated emm55 and MHC II in Neuro-2a Cells. The murine neuroblastoma cell line was transfected with the pcDNA3/emm55 construct containing the complete emm55 gene (FIG. 7). The surface expression of the transfected gene was confirmed by flow cytometry using the 8 F-10 mAb. Twenty one days after electroporation, 10% of the transfected Neuro-2a cells kept under G418 selection were able to bind the 8 F-10 antibody.

For stable expression, Neuro-2a cells were cotransfected with pSGINeopA and pSVK3/emm55 plasmid at 260 V and 1050 µF and kept in culture with G418 for several weeks. Since these conditions were the most efficient in previous electroporations, they were used then for the electroporation of Neuro-2a with pcDV 1/α, pcDV 1/β and pSGINeopA. Stably transfected cells were kept in culture under G418 selection for several weeks.

In Vivo Studies

Example 2

Tumor Cell Inoculation: Untransfected Neuro-2a cells and Neuro-2a cells transfected with emm55 were prepared for inoculation by gently removing them from 75 $cm^2$-tissue culture flasks with a sterile cell scraper. The cell suspension was harvested by centrifugation at 800×g and the resulting pellet resuspended in incomplete IMDM. Seven week-old A/J mice were inoculated subcutaneously in the left flank with Neuro-2a cells. One hundred forty four (144) A/J mice were divided into 2 groups. In the first group, 72 mice were further divided into 4 groups of 18. Each set of 18 mice were injected with the following cell concentrations: $3 \times 10^6$, $1 \times 10^6$, $5 \times 10^5$, and $1 \times 10^5$ in 0.2 ml incomplete IMDM. The mice were examined for tumor development every other day. Once the tumors reached 3.0 cm in diameter, the mice were euthanized. Blood was collected, the spleen harvested and tumors and other tissues were removed from the mice and placed in 10% (w/v) neutral buffered formalin for histological examination. A detailed physical examination was performed at the time the mice were euthanatized.

Effect of Pre-immunization with pcDNA3/emm55-transfected Neuro-2a on Tumor Formation upon Challenge with Untransfected Neuro-2a Cells. Seventeen days post-inoculation, thirty-six A/J mice pre-immunized with pcDNA3/Emm55-transfected Neuro-2a cells, 18 at $3 \times 10^6$ cells and 18 at $1 \times 10^6$ cells, were challenged with $3 \times 10^6$ unmodified Neuro-2a cells. The mice were examined for tumor development every other day. Once the tumors reached 3.0 cm in diameter, the mice were euthanatized. Blood was collected, the spleen harvested and tumors and other tissues were removed from the mice and placed in 10% (w/v) neutral buffered formalin for histological examination. A detailed physical examination was performed at the time the mice were euthanatized. The majority of the mice which failed to develop tumors were not euthanatized.

Tumorgenicity of Neuro-2a in A/J Syngeneic Mice. Adult A/J syngeneic female mice were purchased from The Jackson Laboratory (Bar Harbor, Mass.). All mice were housed in sterile cages, fed with sterile food and water ad libitum, and maintained in a pathogen-free animal facility. For the initial model, mice were injected with predetermined numbers of tumor cells directly under the skin on the right flank, between the front and hind legs. The total volume injected into each mouse was 0.1 ml. Groups of five mice were given different numbers of tumor cells ($3\times10^{10}$, $1\times10^6$, $5\times10^5$ and $1\times10^5$). Results are shown in Table 3.

Neuroblastoma transformed with MHC II and emm55. A neuroblastoma cell line was transformed to express a foreign MHC class II antigen and an Emm55 protein and used to treat a mouse strain in which the neuroblastoma arises. The clone Neuro-2a was established from a spontaneous tumor of strain A albino mouse in 1969. This tumor line, designated C1 300, arose spontaneously in A/J mice and has been carried in this strain since. Neuro-2a resembles human neuroblastoma in many respects and is commonly used and accepted as an experimental model applicable to human use.

TABLE 3

Tumorgenicity of Neuroblastoma Cell Line Neuro-2a in Syngenic A/J Mice

| Neuro-2a Cells × $10^6$ | Mice Injected | Latency (Days) | % Mice With Tumor |
|---|---|---|---|
| 3 | 5 | 7-13 | 100 |
| 1 | 5 | 8-20 | 100 |
| 0.5 | 5 | 10-20 | 80 |
| 0.1 | 5 | 14-28 | 80 |
| 0 | 5 | 0 | 0 |

Neuroblastoma cells were highly tumorigenic in A/J syngeneic mice. Visible tumors appeared at the site of inoculation after a variable latency period. The duration of latency was dependent upon the number of cells injected. Injection of $3\times10^6$ and $1\times10^5$ cells caused tumor formation in 100% of the mice tested, and in these cases, the latency period was 7-20 days. Eighty percent of the mice injected with $5\times10^5$ and $1\times10^5$ cells developed tumors within 10-28 days. Once the tumors appear, they grew rapidly and their size was not dependent on number of cells originally injected.

The tumor grew under the skin, invaded the surrounding muscle tissue and approached 75% r of the weight of the mouse. Resected tumors were soft and well vascularized; angiogenesis of blood vessels was evident. Additionally, in some mice secondary tumor formation was observed. The overwhelming size of the malignant tissue caused necrosis in some of the tumors examined, but on physical examination, there were no neoplasms apparent in other tissues (lung, liver, spleen, bone marrow). Histological examination, however, showed that the metastasis had occurred with microscopic neoplastic foci being present in the lung and the liver but not in the spleen or bone marrow.

Example 3

Figure 8:
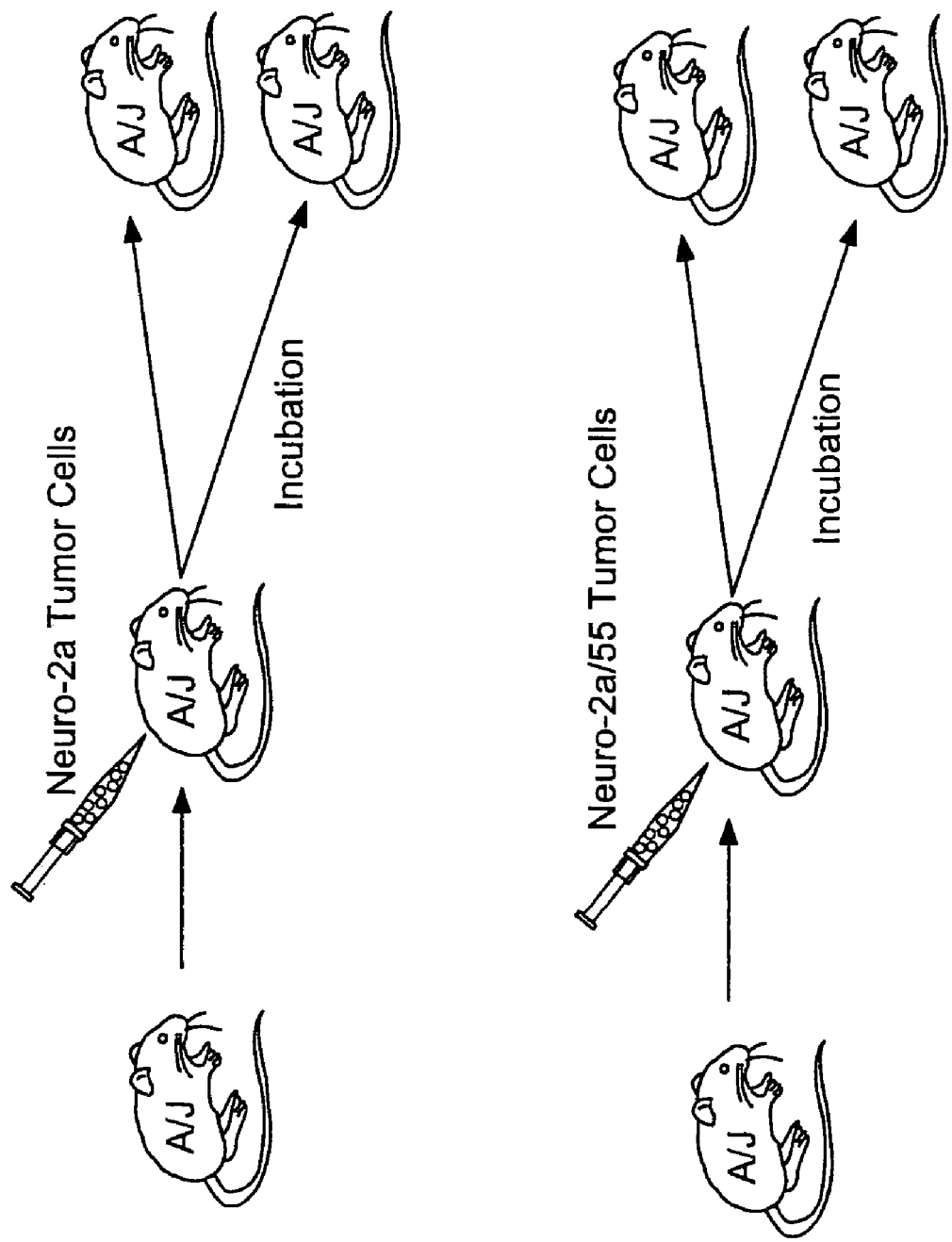
FIG. 8 shows the reduced capacity of Neuro-2a cells expressing Emm55 to produce tumors compared to untransfected Neuro-2a cells. Two groups of 72 mice were inoculated with various doses of Neuro-2a cells and Neuro-2a cells transfected with emm55 (Neuro-2a/55), respectively. Of the 72 mice inoculated with Neuro-2a cells, 64 developed tumors. Of the 72 mice inoculated with Neuro-2a/55, 2 developed tumors. However, these 2 tumors later regressed completely.

Tumorogenicity of pcDNA3/emm55 Transfected Neuro-2a. One hundred forty-four (144) A/J mice were divided into 2 groups. In the first group, 72 of the mice were further divided into 4 groups of 18 and injected with inocula ranging from $3\times10^6$ to $1\times10^5$ unmodified Neuro-2a cells. After 17 days, 89% of the mice had significant tumor development (see Table 4, groups 1-4). Tumors in this group developed rapidly to 2.0-3.0 cm in diameter and by day 24, it was necessary to euthanize all the mice bearing tumors (FIG. 8). The second group of 72 mice were also sub-divided into 4 groups of 18 and injected with inocula ranging from $3\times10^6$ to $1\times10^5$ Neuro-2a neuroblastoma cells which had been had been genetically modified to express Emm55 (N-2a/Emm55). The mice were observed for the appearance of tumors at the site of inoculum. Only two mice, both in the highest inoculum group developed small tumors (<0.5 cm) by day 14. However, these two tumors did not grow and disappeared (regressed) by day 17. Therefore, only 2.8% of the mice given the N-2a/Emm55 cells developed tumors, and they were transient (see Table 4, groups 5-8). All mice receiving modified cells which were not the subject of further experimentation survived to the submission date of this application, i.e., 120 days post-inoculation.

TABLE 4

Tumorogenicity of Neuro-2a and Neuro-2a/Emm55 for A/J mice

| Group | Inoculum | # of Mice Inoculated | # of Mice with Tumors | Day of Onset/ # Tumors Observed |
|---|---|---|---|---|
| 1 | $3 \times 10^6$/N-2a | 18 | 17 | 6/5 |
| 2 | $1 \times 10^6$/N-2a | 18 | 17 | 11/7 |
| 3 | $5 \times 10^5$/N-2a | 18 | 17 | 11/2 |
| 4 | $1 \times 10^5$/N-2a | 28 | 13 | 17/1 |
| | TOTAL | 72 | 64 (89%) | |
| 5 | $3 \times 10^6$/N-2a/Emm55 | 18 | 2* - 0 | 11/2 |
| 6 | $1 \times 10^6$/N-2a/Emm55 | 18 | 0 0 | |
| 7 | $5 \times 10^5$/N-2a/Emm55 | 18 | 0 0 | |
| 8 | $1 \times 10^5$/N-2a/Emm55 | 18 | 0 | 0 |
| | TOTAL | 72 | 2* (2.8%) - 0 | |

N-2a = Neuro-2a tumor cells,
N-2a-Emm55 = Neuro-2a tumor cells expressing Emm55
*Tumors resolved by day 17

Example 4

Tumor Prevention Using the Emm55 Cancer Vaccine

Thirty-six mice were treated with 2 different doses of Neuro-2a cells that had been modified to express Emm55 (N-2a/Emm55) as seen in Table 5. Eighteen control mice received unmodified Neuro-2a cells. At day 17 post inoculation, the mice were challenged with $3\times10^6$ unmodified Neuro-2a cells. The results are shown in Table 5. Seventeen of the 18 control mice receiving unmodified Neuro-2a cells, developed tumors (94%). The tumors reached 2.5-3.0 cm. These mice were euthanatized on day 24. However, 28 of the 36 N-2a/Emm55 pre-immunized mice (78%) were resistant to challenge, i.e., no tumors developed. The tumors of 2 of the 8 mice that did develop tumor regressed completely. The maximum size of the tumors in all of the pre-immunized mice was 1.0-1.5 cm in diameter, half that of the controls. At 100 days post challenge, no further tumors had been observed in mice previously immunized with N-2a/Emm55. Results are shown in Table 5.

TABLE 5

A/J Mice Pre-immunized with Neuro-2a/Emm55 (N-2a/Emm55) are Resistant to Challenge with Neuro-2a

| Group | "Vaccine" Dose | # of Mice | Challenge Dose | # Mice with Tumors | Day of Onset/ # Tumors Observed** |
|---|---|---|---|---|---|
| 1 | $3 \times 10^6$/N-2a/Emm55 | 18 | $3 \times 10^6$/N-2a | 6* (33%) | 7/1 |
| 2 | $1 \times 10^6$/N-2a/Emm55 | 18 | $3 \times 10^6$/N-2a | 2 (11%) | 33/2 |
| 3 | None | 18 | $3 \times 10^6$/N-2a | 17 (94%) | 6/7 |

*2 tumors regressed by day 32 post challenge
**number of mice with tumors on that day The data in FIG. 9, show that without pre-immunization with Neuro-2a/Emm55, mice inoculated with untreated Neuro-2a cells develop tumors within 7 days. The tumors grow rapidly and either kill the mice or necessitate euthanasia. However, tumor production was delayed or totally prevented in mice that had been immunized with either dose of Neuro-2a/Emm55 ($3 \times 10^6$ or $1 \times 10^6$). In 6 of the cases where tumors developed, the tumors failed to exceed 1.5 cm and in two cases, complete regression was observed. No metastases were observed in any of the animals.

Example 5

Humoral Response to Immunization with Tumor Cells Expressing the Emm55 Antigen. Sera drawn from the A/J mice treated as described was used to compare the production of antibodies elicited by inoculation with Neuro-2a/Emm55 cells and unmodified Neuro-2a cells. FIG. 10 is a representation of flow cytometric data where the sera of mice inoculated with Neuro-2a alone showed minimal antibody production to Neuro-2a, while sera from mice inoculated with Neuro-2a/Emm55 produced antibodies specific for Neuro-2a antigens.

Example 6

Therapeutic and Dosage Effects of emm55-transfected Neuro-2a Cells in Mice with Neuroblastoma. The therapeutic efficacy of the emm55-transfected Neuro-2a cell cancer vaccine was dose-dependent. Both vaccine cell number (dosage) and the number of doses (dose rate) affected the development, the onset and the size of tumor development. In this example, 111 syngeneic A/J mice were inoculated with $1 \times 10^6$ Neuro-2a cells. As shown previously, it was known that $1 \times 10^6$ Neuro-2a cells would produce tumors in 95% of A/J mice within 14 days (Table 4) and that once the tumor could be detected, within 10 days the tumor would have advanced to the point where the mice would have to be euthanized.

Figure 11A:
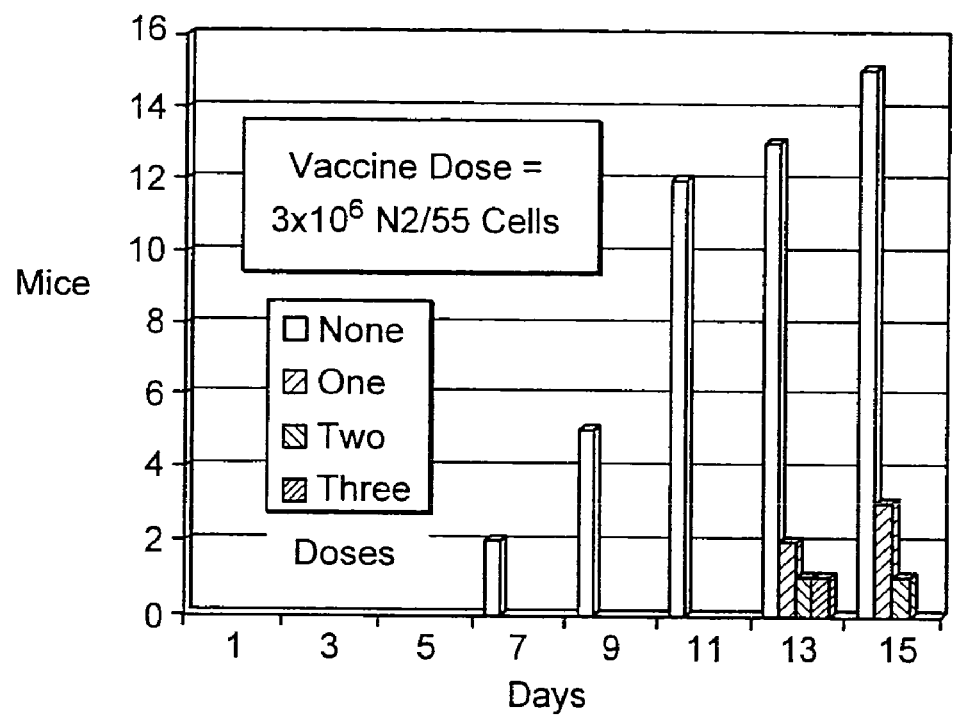
FIG. 11. Therapeutic and Dosage Effects of emm55-transfected Neuro-2a Cells in Mice with Neuroblastoma. One hundred-eleven syngeneic A/J mice were inoculated with $1 \times 10^6$ Neuro-2a cells. These mice were divided into 7 treatment groups. Fifteen mice received no treatment. The remaining 96 mice were divided into 6 groups of 16. Three of these 6 groups received either 1, 2 or 3 inoculations of $3 \times 10^6$ irradiated emm55-transfected Neuro-2a cells on days 3, 8 and 13, respectively (FIG. 11A). The other 3 groups received either 1, 2 or 3 inoculations of $1 \times 10^6$ irradiated emm55-transfected Neuro-2a cells on days 3, 8 and 13, respectively (FIG. 11B). The bars in this graph depict the number of mice which developed tumors by the day indicated. Not presented in this figure are 2 groups of 7 mice which were given 3 doses of either $3 \times 10^6$ or $1 \times 10^6$ irradiated emm55-transfected Neuro-2a cells on days 3, 8 and 13. None of these mice developed tumors.
Figure 11B:
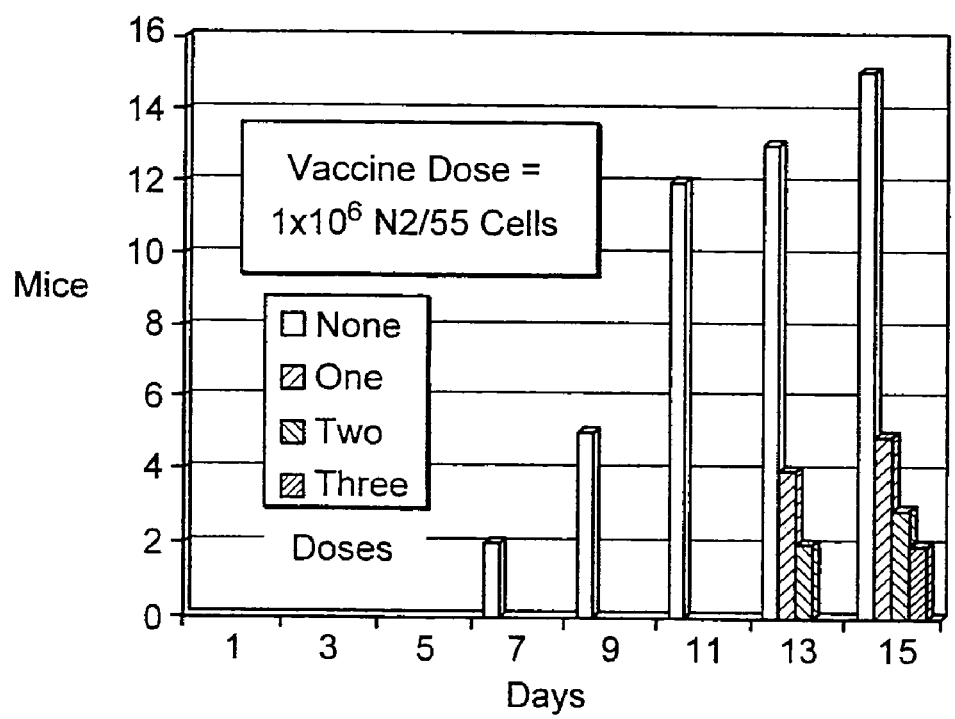

In view of the aggressive nature and predictability of the Neuro-2a/A/J tumor model, treatment was initiated on day three to allow sufficient time for the mice to mount an immune response to the vaccine before the tumor had advanced to a terminal degree. The 111 mice inoculated with wild-type Neuro-2a tumor cells were divided into 7 treatment groups. Fifteen mice received no treatment. The remaining 96 mice were divided into 6 groups of 16. Three of these 6 groups received either 1, 2 or 3 inoculations of $3 \times 10^6$ irradiated emm55-transfected Neuro-2a cells on days 3, 8 and 13, respectively (FIG. 11A). The other 3 groups received either 1, 2 or 3 inoculations of $1 \times 10^6$ irradiated emm55-transfected Neuro-2a cells on days 3, 8 and 13, respectively (FIG. 11B). By day 15, all 15 mice which received no treatment had developed tumors that were between 0.5 and 1.5 cm in diameter.

In contrast, by day 15, none of the 2 groups of 7 mice which were given 3 doses of either $3 \times 10^6$ or $1 \times 10^6$ irradiated emm55-transfected Neuro-2a cells (on days 3, 8 and 13) had developed tumors. No tumors were evident in any of the treated groups until day 13. On that day, 4 out of 16 mice that had received 1 treatment of $1 \times 10^6$ and 2 out of 16 mice that had received 2 treatments of $1 \times 10^6$ cells had developed barely visible tumors. Of the mice receiving $3 \times 10^6$ irradiated emm55-transfected Neuro-2a cells, 2 out of 16 mice which had received a single treatment, 1 out of 16 mice receiving 2 treatments and 1 out of 16 mice receiving 3 treatments had developed tumors. By day 15, the tumor on the mouse which had received 3 treatments at the higher dosage had regressed.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

EP 569678
WO 95/13092
WO 94/21808
WO 96/29093
EP 657168
WO 96/36366, Pore-Forming and Superantigen Encoding Toxin Cassettes for Gene Therapy, (25 Jun. 1993).
WO 95/00178, Gene Therapy for Effector Cell Regulation (29 Dec. 1995).
Banchereau. J., R. M. Steinman (1998) Dendritic cells and the control of immunity. Nature 392: 245-252.
Boyle, M. D P. et al. (1994) Analysis of gene encoding two unique type IIo immunoglobulin G-binding proteins expressed by single group A Streptococcal isolate. Infection and Immunity 62: 1336-1347.
Boyle, M. I. P. et al. (1995) Characterization of a gene coding for a type IIo bacterial IgG-binding protein. Mol. Immunology 9: 669-678.
Cranmer, L. D., Trevor, K. T., and Hersh, E. M., Clinical applications of dendritic cell vaccination in the treatment of cancer. Cancer Immunol Immunother, 53(4), April 275-306 (2004).
Dell, et al. ILAR Journal 43, 2002.
Gibbs, W. W. (2004) Untangling the Roots of Cancer, Scientific American, Vol. 14. Num. 3:60.
Giantonio, et al., Superantigen-based immunotherapy: a phase I trial of PNU-214565, a monoclonal antibody-staphylococccal enterotoxin A recombinant fusion protein, in Advanced pancreatic and colorectal cancer, J. Clin Oncol., 15(5) May 1994-2007 (1997).

Gilboa, L., S. K. Nair, H. K. Byerly (1998) Immunotherapy of cancer with dendritic-cell-based vaccines. *Cancer Immunology and Immunotherapy* 46(2): 82-87.

Hock, R. A. et al. (1996) Murine neuroblastoma vaccines produced by retroviral transfer of MHC class-II genes; major histocompatiblity complex class-II gene transfer to mouse cell culture using a retrovirus vector for cancer gene therapy. *Cancer Gene Ther.* 3(5): 314-320.

Johnson, H. M., J. K. Russell, C. 11. Pontzer (1992) Superantigens in human disease. *Scientific American* (April): 92-101.

Menard. S. et al. (1995) Mycobacterium tuberculosis gene transfer in melanoma cells induces antitumoral immunity in mice; tumor-associated antigen gene transfer and expression in melanoma cell culture for cancer immunotherapy. *Cancer Gene Ther.* 2(4): 318.

Morton, D. L. et al. (1992) Prolongation of survival in metastatic melanoma after active specific immunotherapy with a new polyvalent melanoma vaccine. *Ann Surg.* 216:463.

Okayama, H. et al. (1987) High efficiency cloning of full-length cDNA: construction and screening of cDNA expression libraries for mammalian cells. *Methods in Enzymology* 154: 3-28.

Remington's Pharmaceutical Sciences, 15th

Sambrook, J., E. F. Fritsch, T. Maniatis (1989) *Molecular cloning: A laboratory manual*. Cold Spring Harbor Laboratory Press, Cold Spring Harbor, N.Y.

Sanger, F., S. Niklen, R. A Coulson (1977) DNA sequencing. *Proc Nat Acad. Sci.* 74: 5463-5467.

Soiffer, R. et al. (1998) Vaccination with irradiated autologous melanoma cells engineered to secrete human granulocyte-macrophage colony-stimulating factor generates potent anti-tumor immunity in patients with metastatic melanoma. *Proc. Natl. Acad. Sci. USA*, 95:13141-13146.

Strome, S. et al. (2002) Strategies for antigen loading of dendritic cells to enhance the antitumor immune response. *Cancer Res.*, 62:1884-1889.

Sykes, et al., 1991

Wallach, M., Sivanandham, M., Balch, C. M., et al., A phase II randomized, double-blind multi-institutional trial of vaccinia melanoma oncolysate-active specific immunotherapy for patients with state II melanoma. 1995 Cancer 75: 34-42.

Wang, et al., Int. J. Oncol. 1, July 21, 73-80 (2002).

Yamaguchi, et al., Adoptive immunotherapy of cancer using activated autologous lymphocytes—current status and new strategies. Hum Cell, 16(4) December, 183-189 (2003).

---

What is claimed is:

1. A method for controlling or inhibiting blastoma cancer cell proliferation in a mammal, comprising the steps:
   obtaining a tumor tissue sample from a mammal;
   transforming blastoma cells from said sample with an expression vector comprising a nucleic acid encoding a *Streptococcus pyogenes* Emm55 polypeptide, and administering the transformed cells to the mammal in an amount effective to inhibit or control blastoma cell proliferation.

2. The method of claim 1 wherein the nucleic acid encodes the Emm55 polypeptide selected from the group consisting of a nucleic acid having the sequence of SEQ ID NO. 1 and SEQ ID NO. 2.

3. The method of claim 1 wherein administering the transformed cells causes regression of tumor cells formed by blastoma cell proliferation.

4. The method of claim 1 wherein the blastoma cells are neuroblastoma cells.

5. The method of claim 1 wherein the expression vector further includes a nucleic acid encoding a heterologous MHCII protein.

6. A blastoma cancer cell transformed with an expression vector comprising a nucleic acid encoding a *Streptococcus pyogenes* Emm55 polypeptide.

7. The transformed blastoma cancer cell of claim 6 wherein the Emm55 polypeptide is selected form a group having the nucleic acid sequence of SEQ ID NO. 1 and SEQ ID NO. 2.

8. A blastoma cancer cell population modified to express a *Streptococcus pyogenes* Emm55 polypeptide and a heterologous MHCII polypeptide comprised within a pharmaceutically acceptable vehicle suitable for administration to a subject exhibiting a blastoma type tumor.

9. A blastoma cancer cell vaccine comprising one or a population of autologous mammalian blastoma cells transformed with an expression vector containing a nucleic acid encoding a *Streptococcus pyogenes* Emm55 polypeptide.

10. The vaccine of claim 9 wherein the blastoma cancer cell is a neuroblastoma cell.

11. A pharmaceutical composition comprising the blastoma cancer cell vaccine of claim 9 in a pharmaceutically acceptable excipient.

12. A method for modulating or inhibiting blastoma tumor cell proliferation in a subject comprising administering a therapeutically effective amount of the pharmaceutical composition of claim 11 to a subject suffering from a blastoma cancer.

13. An expression vector comprising a nucleic acid encoding a *Streptococcus pyogenes* Emm55 polypeptide and a nucleic acid encoding a MHCII polypeptide.

* * * * *

SEQUENCE LISTING

```
<160> NUMBER OF SEQ ID NOS: 6

<210> SEQ ID NO 1
<211> LENGTH: 850
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 1
ctgtggaatg tgtgtcagtt agggtgtgga aagtccccag gctccccagc aggcagaagt      60
atgcaaagca tgcatctcaa ttagtcagca accaggtgtg gaaagtcccc aggctcccca     120
gcaggcagaa gtatgcaaag catgcatctc aattagtcag caaccatagt cccgccccta     180
actccgccca tcccgcccct aactccgccc agttccgccc attctccgcc ccatggctga     240 ctaattttt ttatttatgc agaggccgag gccgcctcgg cctctgagct attccagaag      300
tagtgaggag gcttttttgg aggcctaggc ttttgcaaaa agctatcgaa ttaatacgac      360
tcattatagg gagatcgaat tcggcwtggc taaaaatacc acgaatagac ackattcgct      420
tagaaaatta aaaacaggaa cggcttcagt agcagtagct ttgactgttt tgggacagg      480 actggtagca gggcagacag taaaagcaaa ccaaacagaa ccatctcaga ccaataacag     540
attatatcaa gaaagacaac gtttacagga tttaaaaagt aagtttcaag acctgaaaaa     600
tcgttcagag ggatacattc agcaatacta cgacgaagaa aagaacagtg gaagtaactc     660
taactggtac gcaacctact taaaagaatt aaatgacgaa tttgaacaag cttataatga     720
acttagtggt gatggtgtaa aaaaattagc tgcaagtttg atggaagaaa gagtcgcttt     780
aagagacgaa atcgatcaga ttatgaaaat atcagaagaa ttaaaaaata agctgagagc     840
aacagaagaa                                                            850

<210> SEQ ID NO 2
```

<211> LENGTH: 847
<212> TYPE: DNA
<213> ORGANISM: Artificial Sequence
<220> FEATURE:
<223> OTHER INFORMATION: Description of Artificial Sequence: Synthetic
      pSVK3/emm55 construct sequence

<400> SEQUENCE: 2

```
ctgtggaatg tgtgtcagtt agggtgtgga aagtccccag gctccccagc aggcagaagt      60
atgcaaagca tgcatctcaa ttagtcagca accaggtgtg aaagtcccc aggctcccca     120 gcaggcagaa gtatgcaaag catgcatctc aattagtcag caaccatagt cccgccccta    180
actccgccca tcccgcccct aactccgccc agttccgccc attctccgcc ccatggctga    240
ctaatttttt ttatttatgc agaggccgag gccgcctcgg cctctgagct attccagaag    300
tagtgaggag gcttttttgg aggcctaggc ttttgcaaaa agctatcgaa ttaatacgac    360
tcattatagg gagatcgaat tcatggctaa aataccacg aatagacacg attcgcttag     420
aaaattaaaa acaggaacgg cttcagtagc agtagctttg actgttttg ggacaggact     480 ggtagcaggg cagacagtaa aagcaaacca acagaacca tctcagacca ataacagatt     540
atatcaagaa agacaacgtt tacaggattt aaaaagtaag tttcaagacc tgaaaaatcg    600
ttcagaggga tacattcagc aatactacga cgaagaaaag aacagtggaa gtaactctaa    660
ctggtacgca acctacttaa aagaattaaa tgacgaattt gaacaagctt ataatgaact    720
tagtggtgat ggtgtaaaaa aattagctgc aagtttgatg gaagaaagag tcgctttaag    780
agacgaaatc gatcagatta tgaaaatatc agaagaatta aaaataagc tgagagcaac     840 agaagaa                                                              847
```

<210> SEQ ID NO 3
<211> LENGTH: 178
<212> TYPE: DNA
<213> ORGANISM: Streptococcus pyogenes

<400> SEQUENCE: 3

```
tttgcaaaaa gctatcgaat taatacgact cattataggg agatcgaatt cggcttggct      60
aaaaatacca cgaatagaca ctattcgctt agaaaattaa aaacaggaac ggcttcagta    120
gcagtagctt tgactgtttt tgggacagga ctggtagcag ggcagacagt aaaagcaa      178
```

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
tagaattcat ggctaaaaat accacgaata g                                    31
```

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
ttctcgagtt agtttttcttc tttgcgtttg ac                                  32
```

```
<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagttccgcc cattcttc                                                   18
```